US010390788B2

(12) United States Patent
Kravis et al.

(10) Patent No.: US 10,390,788 B2
(45) Date of Patent: Aug. 27, 2019

(54) MULTIPLE-DIMENSION IMAGING SENSOR WITH OPERATION BASED ON DETECTION OF PLACEMENT IN MOUTH

(71) Applicant: DENTAL IMAGING TECHNOLOGIES CORPORATION, Hatfield, PA (US)

(72) Inventors: Scott David Kravis, Lambertville, NJ (US); Leonid Khatutskiy, Washington Crossing, PA (US); James Paul Frerichs, Sellersville, PA (US); Adrian David French, Suno (IT); Kyle Alan Pixton, Lansdale, PA (US)

(73) Assignee: DENTAL IMAGING TECHNOLOGIES CORPORATION, Hatfield, PA (US)

( * ) Notice: Subject to any disclaimer, the term of this patent is extended or adjusted under 35 U.S.C. 154(b) by 0 days.

(21) Appl. No.: 16/282,646

(22) Filed: Feb. 22, 2019

(65) Prior Publication Data
US 2019/0183449 A1 Jun. 20, 2019

Related U.S. Application Data

(63) Continuation of application No. 15/627,199, filed on Jun. 19, 2017, now Pat. No. 10,213,180, which is a (Continued)

(51) Int. Cl.
*A61B 6/00* (2006.01)
*A61B 6/14* (2006.01)
(Continued)

(52) U.S. Cl.
CPC .............. *A61B 6/547* (2013.01); *A61B 5/01* (2013.01); *A61B 6/145* (2013.01); *A61B 6/4233* (2013.01);
(Continued)

(58) Field of Classification Search
CPC ......... A61B 6/547; A61B 6/145; A61B 6/465; A61B 5/01; A61B 6/587; A61B 6/586;
(Continued)

(56) References Cited

U.S. PATENT DOCUMENTS 4,223,228 A * 9/1980 Kaplan ................. A61B 6/08 324/207.2
5,463,669 A 10/1995 Kaplan
(Continued)

FOREIGN PATENT DOCUMENTS

CN 105142322 A 12/2015
EP 2302451 A1 3/2011
(Continued)

OTHER PUBLICATIONS

Office Action from the U.S. Patent and Trademark Office for U.S. Appl. No. 15/265,753 dated Nov. 3, 2017 (32 pages).
(Continued)

*Primary Examiner* — Taeho Jo
(74) *Attorney, Agent, or Firm* — Michael Best & Friedrich LLP

(57) ABSTRACT

Methods and systems are described for operating an intra-oral imaging sensor that includes a housing, an image sensing component at least partially housed within the housing, and a temperature sensor. An output of the temperature indicative of a sensed temperature is received and evaluated to determine whether the intra-oral imaging sensor is positioned in the mouth of the patient. The determination of whether the temperature sensor may be based on one or more determined conditions including whether a current temperature exceeds a threshold, whether a first derivative of the sensed temperature exceeds a rate-of-change threshold, and whether a second derivative of the sensed temperature exceeds a temperature acceleration threshold. In some
(Continued)

implementations, the operation of the intra-oral imaging sensor is automatically adjusted in response to a determination that the sensor has been placed inside the mouth of a patient.

20 Claims, 15 Drawing Sheets

Related U.S. Application Data continuation-in-part of application No. 15/265,753, filed on Sep. 14, 2016.

(51) Int. Cl.

| | | |
|---|---|---|
| G03B 42/04 | (2006.01) | |
| H01H 35/14 | (2006.01) | |
| H01L 27/14 | (2006.01) | |
| H01L 31/00 | (2006.01) | |
| G06F 3/01 | (2006.01) | |
| G06F 1/3234 | (2019.01) | |
| G06F 1/3206 | (2019.01) | |
| G06F 1/3203 | (2019.01) | |
| G06F 1/32 | (2019.01) | |
| G01R 31/02 | (2006.01) | |
| G01R 33/02 | (2006.01) | |
| G01L 7/00 | (2006.01) | |
| A61B 5/01 | (2006.01) | |
| H01H 36/00 | (2006.01) | |
| G01T 1/16 | (2006.01) | |

(52) U.S. Cl.
CPC .......... *A61B 6/4405* (2013.01); *A61B 6/465* (2013.01); *A61B 6/467* (2013.01); *A61B 6/586* (2013.01); *A61B 6/587* (2013.01); *G01L 7/00* (2013.01); *G01R 31/02* (2013.01); *G01R 33/02* (2013.01); *G03B 42/042* (2013.01); *G06F 1/32* (2013.01); *G06F 1/3203* (2013.01); *G06F 1/3206* (2013.01); *G06F 1/3234* (2013.01); *G06F 3/017* (2013.01); *H01H 35/14* (2013.01); *H01H 36/00* (2013.01); *H01L 27/14* (2013.01); *H01L 31/00* (2013.01); *A61B 6/4429* (2013.01); *A61B 2560/0204* (2013.01); *G01T 1/16* (2013.01)

(58) Field of Classification Search
CPC ..... A61B 6/467; A61B 6/4405; A61B 6/4233; A61B 6/4429; A61B 2560/0204; G03B 42/042; H01H 35/14; H01H 36/00; H01L 27/14; H01L 31/00; G06F 3/017; G06F 1/3234; G06F 1/3206; G06F 1/3203; G06F 1/32; G01R 31/02; G01R 33/02; G01L 7/00; G01T 1/16
USPC ........................................................ 250/362
See application file for complete search history.

(56) References Cited

U.S. PATENT DOCUMENTS

| | | | |
|---|---|---|---|
| 5,661,519 A | 8/1997 | Franetzki | |
| 5,887,049 A | 3/1999 | Fossum | |
| 6,122,538 A | 9/2000 | Sliwa, Jr. et al. | |
| 6,924,486 B2 | 8/2005 | Schick et al. | |
| 7,016,468 B1* | 3/2006 | Krema | H05G 1/34 378/101 |
| 7,503,692 B2 | 3/2009 | De Godzinsky | |
| 7,588,369 B2 | 9/2009 | Varjonen et al. | |
| 7,599,538 B2 | 10/2009 | Crucs | |
| 7,986,415 B2 | 7/2011 | Thiel et al. | |
| 7,988,356 B2 | 8/2011 | Watanabe | |
| 7,997,796 B2 | 8/2011 | De Godzinsky | |
| 8,149,990 B2 | 4/2012 | De Godzinsky | |
| 8,324,587 B2 | 12/2012 | Zeller | |
| 8,519,348 B2 | 8/2013 | Topfer et al. | |
| 8,690,426 B2 | 4/2014 | Liu et al. | |
| 9,216,003 B1 | 12/2015 | Chen et al. | |
| 9,314,216 B2 | 4/2016 | De Godzinsky et al. | |
| 2001/0055368 A1* | 12/2001 | Carroll | A61B 6/14 378/189 |
| 2002/0015934 A1 | 2/2002 | Rubbert et al. | |
| 2003/0194056 A1 | 10/2003 | Spahn | |
| 2004/0218792 A1 | 11/2004 | Spoonhower et al. | |
| 2004/0238721 A1* | 12/2004 | Miyaguchi | A61B 6/4233 250/208.1 |
| 2005/0207534 A1 | 9/2005 | Petrick et al. | |
| 2006/0257816 A1 | 11/2006 | Klemola et al. | |
| 2007/0065782 A1* | 3/2007 | Maschke | A61C 13/0004 433/224 |
| 2007/0153980 A1 | 7/2007 | Butzine et al. | |
| 2007/0223649 A1 | 9/2007 | De Godzinsky | |
| 2007/0286335 A1 | 12/2007 | De Godzinsky | |
| 2008/0002808 A1 | 1/2008 | De Godzinsky | |
| 2008/0019579 A1* | 1/2008 | Crucs | A61B 6/145 382/128 |
| 2008/0130837 A1 | 6/2008 | Heath et al. | |
| 2008/0234935 A1 | 9/2008 | Wolf et al. | |
| 2010/0007725 A1 | 1/2010 | Crucs | |
| 2010/0102241 A1 | 4/2010 | Zeller | |
| 2010/0161084 A1 | 6/2010 | Zhao et al. | |
| 2011/0051902 A1 | 3/2011 | Liu et al. | |
| 2011/0192966 A1 | 8/2011 | Harada et al. | |
| 2011/0228075 A1 | 9/2011 | Madden et al. | |
| 2011/0305319 A1 | 12/2011 | Liu et al. | |
| 2012/0041298 A1* | 2/2012 | Mersky | H04R 25/554 600/410 |
| 2012/0230473 A1 | 9/2012 | Stagnitto et al. | |
| 2012/0288819 A1 | 11/2012 | Burrell et al. | |
| 2012/0307965 A1 | 12/2012 | Bothorel et al. | |
| 2013/0034213 A1 | 2/2013 | Liu et al. | |
| 2013/0043400 A1 | 2/2013 | Nakatsugawa et al. | |
| 2013/0064346 A1* | 3/2013 | Ferren | G01N 23/04 378/62 |
| 2013/0092844 A1 | 4/2013 | Zeller | |
| 2013/0140289 A1 | 6/2013 | Baratier et al. | |
| 2013/0142309 A1 | 6/2013 | Iwakiri et al. | |
| 2014/0005555 A1* | 1/2014 | Tesar | A61B 17/02 600/476 |
| 2014/0010349 A1 | 1/2014 | De Godzinsky et al. | |
| 2014/0010350 A1 | 1/2014 | De Godzinsky et al. | |
| 2014/0086389 A1* | 3/2014 | Baek | A61B 6/587 378/62 |
| 2014/0146142 A1 | 5/2014 | Duret et al. | |
| 2014/0152464 A1 | 6/2014 | Smith | |
| 2014/0198901 A1 | 7/2014 | Christoff | |
| 2014/0199649 A1 | 7/2014 | Apte et al. | |
| 2014/0199650 A1 | 7/2014 | Moffson et al. | |
| 2014/0215235 A1 | 7/2014 | Lipasti et al. | |
| 2014/0254760 A1* | 9/2014 | Hiroike | A61B 6/4233 378/62 |
| 2014/0272772 A1 | 9/2014 | Andreiko et al. | |
| 2014/0342324 A1* | 11/2014 | Ghovanloo | G09B 5/06 434/185 |
| 2014/0347274 A1* | 11/2014 | Koh | G06F 3/0346 345/158 |
| 2014/0351558 A1 | 11/2014 | Burca et al. | |
| 2014/0351559 A1* | 11/2014 | Lautner | G06F 3/0346 712/30 |
| 2014/0351560 A1* | 11/2014 | Lautner | G06F 3/0346 712/30 |
| 2015/0168566 A1 | 6/2015 | Shikino et al. | |
| 2015/0238073 A1* | 8/2015 | Charles | A61B 17/02 600/102 |
| 2015/0250433 A1* | 9/2015 | Hyde | A61B 6/145 378/62 |
| 2015/0250435 A1* | 9/2015 | Hyde | A61B 6/145 378/62 |

(56) References Cited

U.S. PATENT DOCUMENTS

| | | | |
|---|---|---|---|
| 2015/0250436 A1* | 9/2015 | Hyde | A61B 6/145 378/62 |
| 2015/0306340 A1* | 10/2015 | Giap | G16H 40/63 600/301 |
| 2015/0333535 A1 | 11/2015 | Feine | |
| 2015/0342558 A1* | 12/2015 | Kwak | A61B 6/548 378/62 |
| 2015/0350517 A1 | 12/2015 | Duret et al. | |
| 2016/0033424 A1 | 2/2016 | Ferren | |
| 2016/0100908 A1 | 4/2016 | Tesar | |
| 2016/0128624 A1* | 5/2016 | Matt | A61C 19/045 600/301 |
| 2016/0135779 A1* | 5/2016 | Kim | A61B 6/547 378/116 |
| 2016/0143609 A1* | 5/2016 | Park | A61B 6/547 378/98.2 |
| 2016/0143611 A1 | 5/2016 | Ota et al. | |
| 2016/0262715 A1* | 9/2016 | Charnegie | A61B 6/545 |
| 2016/0262716 A1* | 9/2016 | Kravis | A61B 6/463 |
| 2016/0310077 A1* | 10/2016 | Hunter | A61B 5/0024 |
| 2017/0027532 A1 | 2/2017 | Joshi et al. | |
| 2017/0035383 A1 | 2/2017 | Liu et al. | |
| 2017/0128030 A1 | 5/2017 | Kong et al. | |
| 2017/0300119 A1* | 10/2017 | Wu | A61B 6/145 |

FOREIGN PATENT DOCUMENTS

| | | |
|---|---|---|
| EP | 3066984 A2 | 9/2016 |
| JP | S605124 A | 1/1985 |
| JP | 2009291316 A | 12/2009 |
| JP | 2012045242 A | 3/2012 |
| JP | 2014032158 A | 2/2014 |
| WO | WO 2010150148 A1 | 12/2010 |
| WO | WO 2012033029 A1 | 3/2012 |
| WO | WO 2012087161 A1 | 6/2012 |
| WO | WO 2014100950 A1 | 7/2014 |
| WO | WO 2015196388 A1 | 12/2015 |

OTHER PUBLICATIONS

International Search Report and Written Opinion for Application No. PCT/US2017/051416 dated Dec. 6, 2017 (15 pages).
International Search Report and Written Opinion for Application No. PCT/US2017/051417 dated Dec. 7, 2017 (14 pages).
International Search Report and Written Opinion for Application No. PCT/US2017/051418 dated Dec. 6, 2017 (13 pages).
International Search Report and Written Opinion for Application No. PCT/US2017/051420 dated Dec. 6, 2017 (13 pages).
Non-Final Office Action from the U.S. Patent and Trademark Office for U.S. Appl. No. 15/627,232 dated May 9, 2018 (26 pages).
Non-Final Office Action from the U.S. Patent and Trademark Office for U.S. Appl. No. 15/627,245 dated May 23, 2018 (19 pages).
Non-Final Office Action from the U.S. Patent and Trademark Office for U.S. Appl. No. 15/265,753 dated Aug. 13, 2018 (29 pages).
Final Office Action from the U.S. Patent and Trademark Office for U.S. Appl. No. 15/627,232 dated Nov. 6, 2018 (27 pages).
Notice of Allowance from the U.S. Patent and Trademark Office for U.S. Appl. No. 15/627,245 dated Jan. 10, 2019 (14 pages).
Notice of Allowance from the U.S. Patent and Trademark Office for U.S. Appl. No. 15/627,199 dated Oct. 11, 2018 (17 pages).
Non-Final Office Action from the U.S. Patent and Trademark Office for U.S. Appl. No. 15/265,753 dated Aug. 13, 2018 (27 pages).
Non-Final Office Action from the U.S. Patent and Trademark Office for U.S. Appl. No. 15/627,199 dated Apr. 10, 2018 (20 pages).
International Preliminary Report on Patentability for Application No. PCT/US2017/051416 dated Mar. 28, 2019 (9 pages).
International Preliminary Report on Patentability for Application No. PCT/US2017/051417 dated Mar. 28, 2017 (8 pages).
International Preliminary Report on Patentability for Application No. PCT/US2017/051418 dated Mar. 28, 2019 (7 pages).
International Preliminary Report on Patentability for Application No. PCT/US2017/051420 dated Mar. 28, 2019 (7 pages).

* cited by examiner

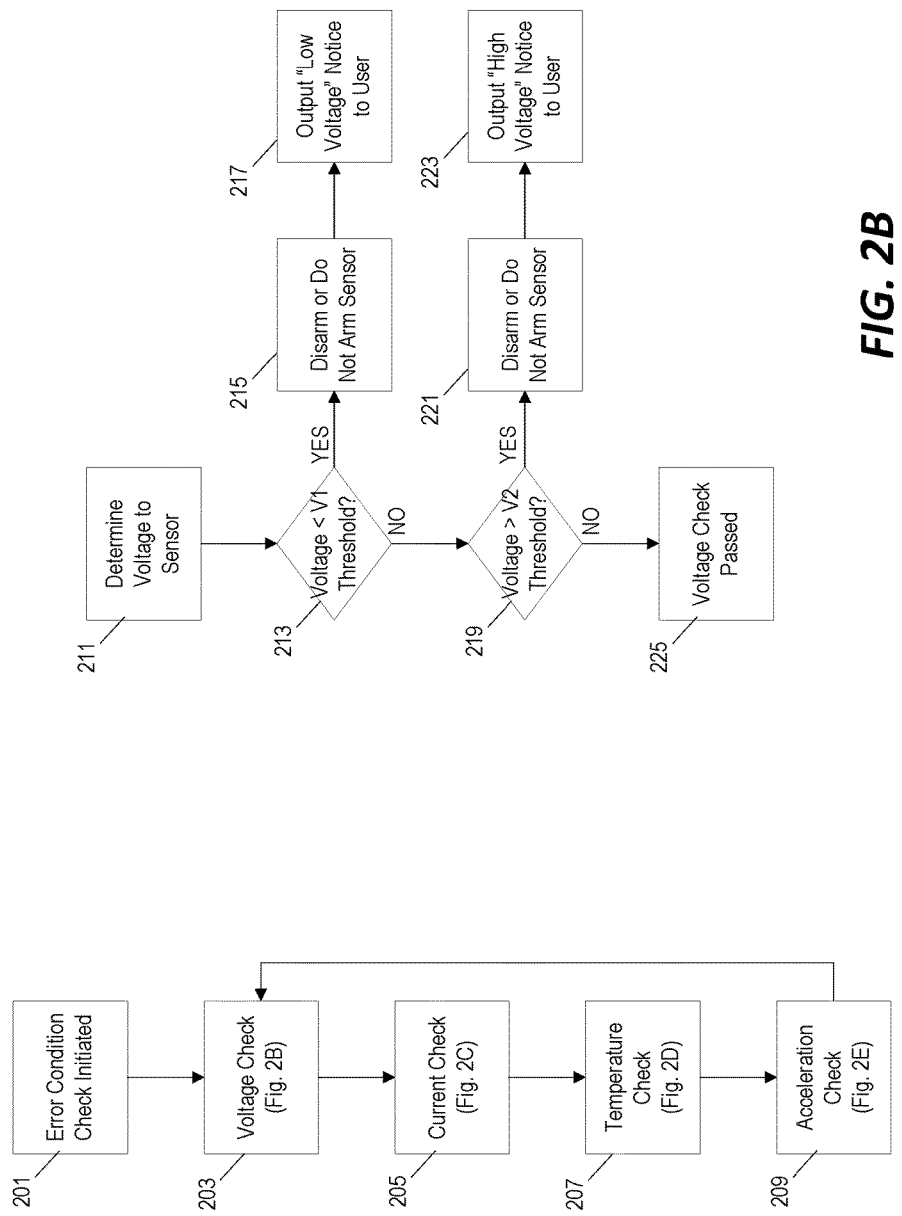

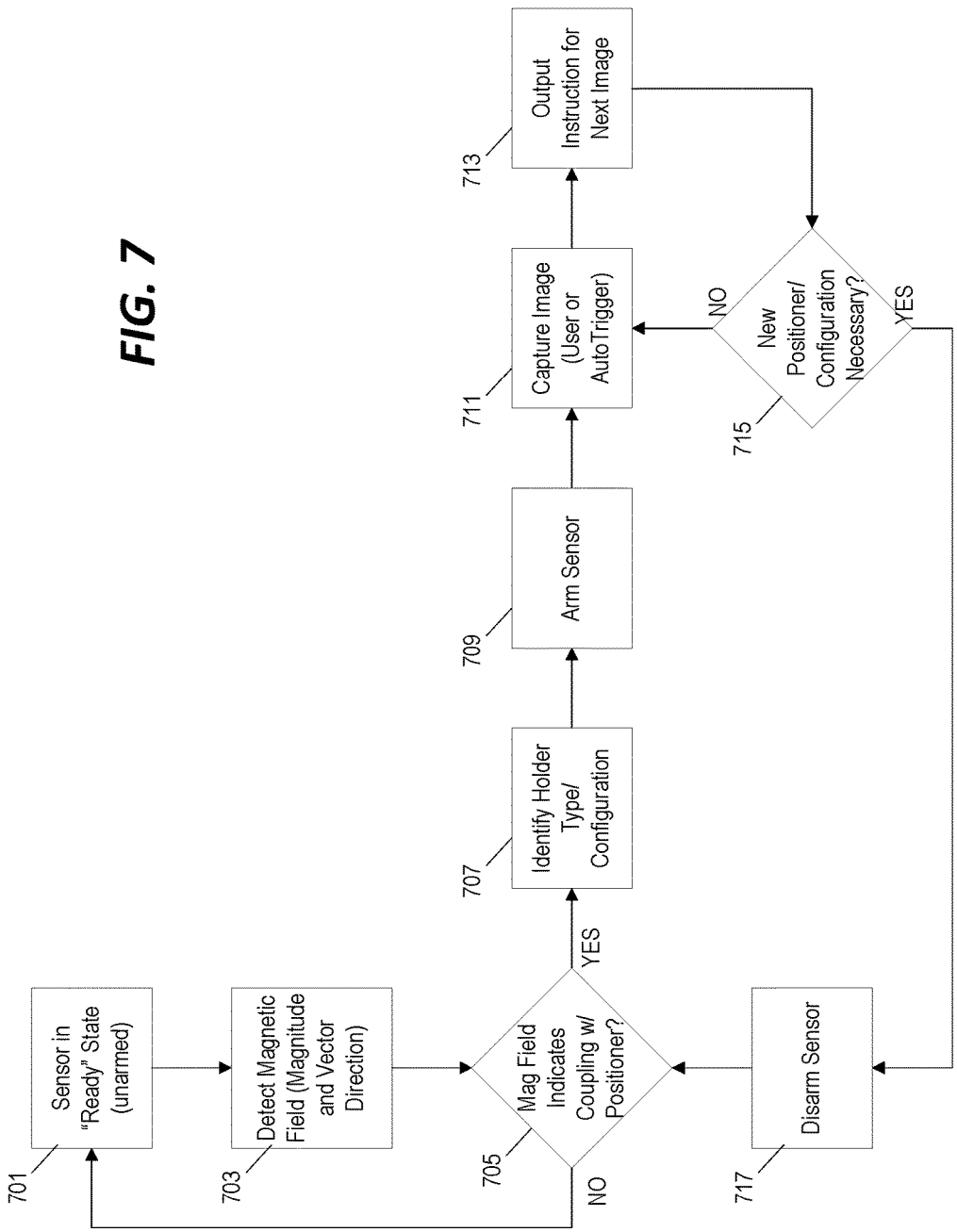

MULTIPLE-DIMENSION IMAGING SENSOR WITH OPERATION BASED ON DETECTION OF PLACEMENT IN MOUTH

RELATED APPLICATIONS

This application is a continuation of U.S. patent application Ser. No. 15/627,199, filed Jun. 19, 2017, entitled "MULTIPLE-DIMENSION IMAGING SENSOR WITH OPERATION BASED ON MAGNETIC FIELD DETECTION," which is a continuation-in-part of U.S. application Ser. No. 15/265,753, filed Sep. 14, 2016, entitled "MULTIPLE-DIMENSION IMAGING SENSOR AND STATE-BASED OPERATION OF AN IMAGING SYSTEM INCLUDING A MULTIPLE-DIMENSION IMAGING SENSOR," the entire contents of both of which are incorporated herein by reference.

BACKGROUND

Embodiments relate to systems and methods for capturing images using a sensor.

X-ray imaging systems often include a sensor for detecting x-ray radiation that has passed through an object of interest or structure. For example, in dental applications, an intra-oral sensor may be positioned in the mouth of a patient. X-ray radiation is directed at the object of interest and toward the sensor. Data output from the intra-oral sensor is processed to generate an x-ray image of the object of interest, for example, one or more teeth or other dental structures.

SUMMARY

In some instances, a multi-dimensional sensor is incorporated into an intra-oral x-ray sensor (sometimes referred to as an "imaging sensor"). The multi-dimensional sensor can include, for example, a three-dimensional accelerometer, a three-dimensional gyroscopic sensor, and a three-dimensional magnetometer to provide nine-dimensions of positional and movement information for the imaging sensor. In some instances, additional or alternative sensors may also be incorporated into the imaging sensor including, for example, a temperature sensor, a current/voltage sensor or monitoring circuit, and an air pressure sensor.

Among other things, an imaging sensor equipped with a multi-dimensional sensor can be used to determine when the imaging sensor is properly aligned with an x-ray source and with a dental structure to be imaged. In addition, information provided by the multi-dimensional sensor can be used by an imaging system to determine when to arm the imaging sensor, to determine the "health" of the imaging sensors, and, in some implementations, when to place the imaging sensor in a "low power" mode.

In one embodiment, the invention provides a method for operating an imaging sensor, the imaging sensor including a multi-dimensional sensor. An electronic processor receives an output from the multi-dimensional sensor and transitions the imaging sensor from a first operating state into a second operating state in response to a determination by the electronic processor, based on the output from the multi-dimensional sensor, that a first state transition criteria is satisfied.

In another embodiment, the invention provides a method for operating an imaging sensor, the imaging sensor including a multi-dimensional sensor. An electronic processor operates the imaging sensor in a low-power state. In some embodiments, while operating in the low-power state, the imaging sensor does not capture any image data and is not able to transition directly into an "armed" state in which image data is captured. The electronic processor receives an output from the multi-dimensional sensor and transitions the imaging sensor from the low-power state into a ready state in response to a determination by the electronic processor, based on the output from the multi-dimensional sensor, that a first state transition criteria is satisfied. The electronic processor also transitions the imaging sensor from the ready state into an armed state in response to a determination made by the electronic processor, based on the output from the multi-dimensional sensor, that a second state transition criteria is satisfied. The electronic processor operates the imaging sensor to capture image data only when operating in the armed state and does not transition from the low-power state directly into the armed state based on automated state transition criteria from the multi-dimensional sensor.

In yet another embodiment, the invention provides an imaging system that includes an intra-oral imaging sensor and an electronic processor. The intra-oral imaging sensor includes a housing, an image sensing component at least partially housed within the housing, and a magnetometer at least partially housed within the housing. The electronic processor is configured to receive an output of the magnetometer indicative of an actual magnetic field that impinges the intra-oral imaging sensor. The electronic processor compares the data indicative of the actual magnetic field based on the output of the magnetometer to data indicative of a first expected magnetic field. In response to determining, based on the comparison, that the actual magnetic field matches the first expected magnetic field, the electronic processor alters the operation of the imaging system. In some embodiments, the electronic processor causes the intra-oral imaging sensor to operate in a low-power state in response to determining that the actual magnetic field matches a first expected magnetic field indicative of placement of the intra-oral imaging sensor in an imaging sensor storage compartment.

In some embodiments, the invention provides an imaging system that includes an intra-oral imaging sensor and an electronic processor. The intra-oral imaging sensor includes a housing, an image sensing component at least partially housed within the housing, and a multi-dimensional sensor at least partially housed within the housing. The electronic processor is configured to receive an output of the multi-dimensional sensor indicative of movement of the intra-oral imaging sensor. The output is compared to predetermined movement criteria indicative of a type of movement and, in response to determining that the type of movement of the imaging sensor has occurred, the electronic processor alters the operation of the imaging system.

In still other embodiments, the invention provides an imaging system that includes an intra-oral imaging sensor, an image sensing component, a multi-dimensional sensor, and an electronic processor. The intra-oral imaging sensor includes a housing and the image sensor component and the multi-dimensional sensor are at least partially housed within the housing. The multi-dimensional sensor includes a three-dimensional accelerometer, a three-dimensional gyroscope, and a three-dimensional magnetometer. The electronic processor is configured to execute one or more error condition check routines to determine whether an error condition is present based on an output received from the multi-dimensional sensor.

Other aspects of the invention will become apparent by consideration of the detailed description and accompanying drawings.

BRIEF DESCRIPTION OF THE DRAWINGS

FIG. 2A is a flowchart of method for checking a sensor for errors performed by the imaging system of FIG. 1A.

FIG. 2B is a flowchart of a method for checking the sensor voltage in the method of FIG. 2A.

FIG. 7 is a flowchart of a method for transitioning between operating states of the imaging system of FIG. 1A based on a detection of a coupling between the imaging sensor and a sensor holder of FIG. 6.

DETAILED DESCRIPTION

Before any embodiments are explained in detail, it is to be understood that the invention is not limited in its application to the details of construction and the arrangement of components set forth in the following description or illustrated in the following drawings. Other embodiments and ways of being practiced or of being carried out are possible.

Figure 1A:
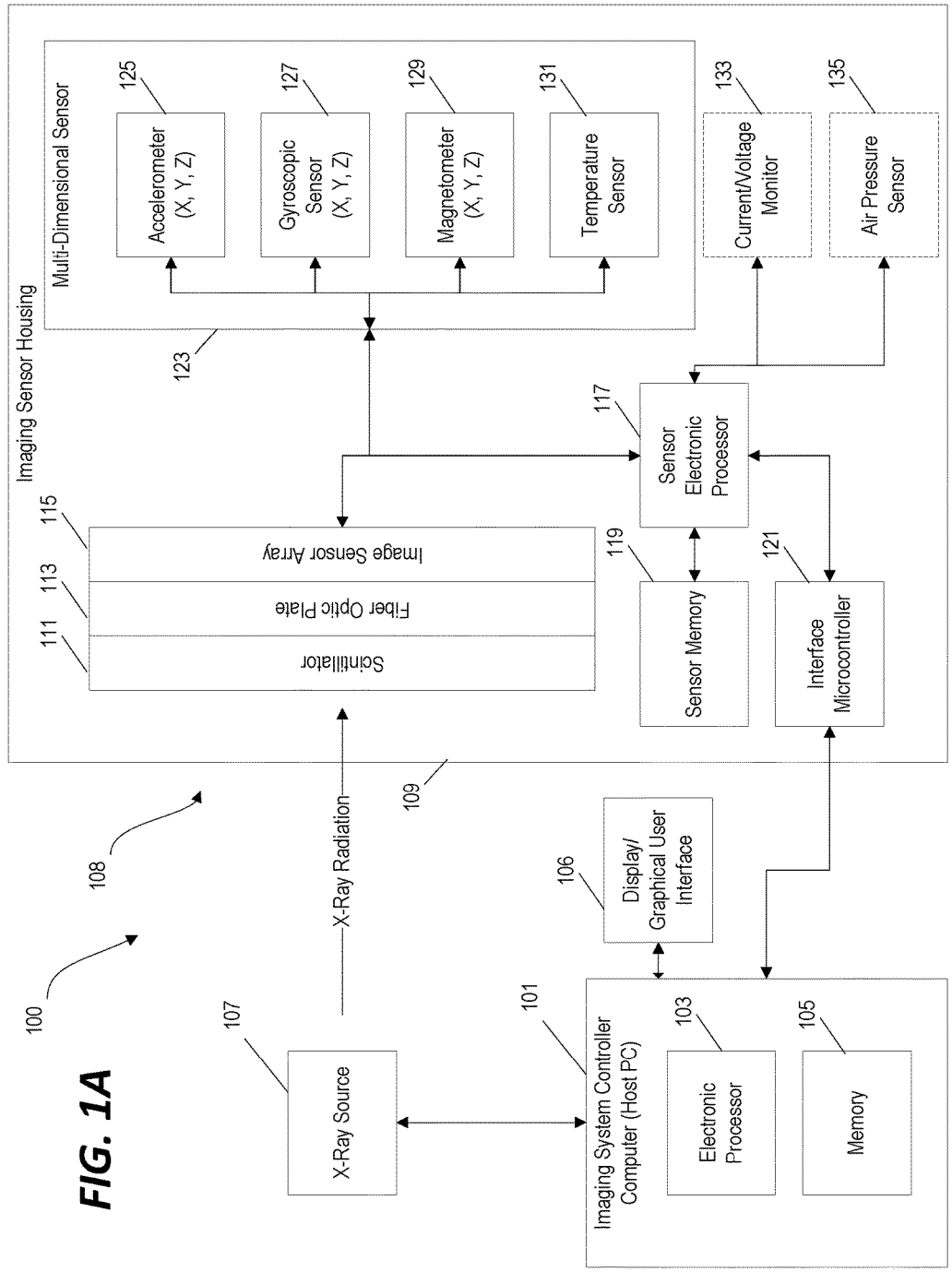
FIG. 1A is a block diagram of an imaging system including a multi-dimensional sensor integrated into the imaging sensor housing according to one embodiment.

FIG. 1A illustrates an example of an imaging system 100. In the examples discussed herein, the imaging system 100 is a dental imaging system for use with an intra-oral imaging sensor. However, in other implementations, the imaging system 100 may be configured for other medical or non-medical imaging purposes. The imaging system 100 includes an imaging system controller computer 101, which, in some implementations, includes software executed on a personal computer, tablet computer, or other computing device. The imaging system controller computer 101 includes an electronic processor 103 and a memory 105. In one example, all or part of the memory 105 is non-transitory and computer readable and stores instructions that are executed by the electronic processor 103 to provide the functionality of the imaging system controller computer 101, for example, as presented in this disclosure.

In the example of FIG. 1A, the imaging system controller computer 101 is communicatively coupled to a display 106. The system controller computer 101 generates a graphical user interface that is output on the display 106. As discussed in greater detail below, the graphical user interface is configured to receive various inputs from a user and to output instructions, data, and other information to the user. Although the display 106 is shown as a separate unit coupled to the imaging system controller computer 101 in the example of FIG. 1A, in other implementations, the display 106 is integrated into the same housing as the imaging system controller computer 101, for example, where the imaging system controller computer 101 is implemented as a laptop computer or a tablet computer.

In the example of FIG. 1A, the imaging system controller computer 101 is communicatively coupled to an x-ray source 107 and an imaging sensor 108. The imaging sensor 108—in this example, an intra-oral dental imaging sensor—includes an imaging sensor housing 109. An image sensing component is positioned within the imaging sensor housing 109 and is configured to capture data that is then used to generate an image. The example of FIG. 1A includes a scintillator 111, a fiber optic plate 113, and an image sensor array 115 as the image sensing component positioned within the imaging sensor housing. In response to receiving x-ray radiation, the scintillator 111 produces photons that pass through the fiber optic plate 113. The image sensor array 115 detects the photons directed by the fiber optic plate 113 and outputs data used to generate an x-ray image. Other implementations may include other image detection components including, for example, a direct conversion detector (e.g., a photon counter) that is configured to operate without a scintillator and/or a fiber optic plate.

A sensor electronic processor 117 is also positioned within the imaging sensor housing 109 and is communicatively coupled to the image sensor array 115 to receive signals indicative of the detected x-ray radiation. In some implementations, the sensor electronic processor 117 is also coupled to a sensor memory 119. In certain embodiments, the sensor electronic processor 117 is provided as a field programmable gate array while, in other embodiments, the sensor electronic processor 117 is a different type of processor and the sensor memory 119 is a non-transitory computer-readable memory which stores instructions that are executed by the sensor electronic processor 117 to provide or perform certain functions as described herein.

In the example of FIG. 1A, the sensor electronic processor 117 is communicatively coupled with an interface microcontroller 121. In the example illustrated, the interface microcontroller 121 is also positioned within the imaging sensor housing 109 and is configured to provide communication between the sensor electronic processor 117 and the imaging system controller computer 101 as discussed in greater detail below. In some implementations, the imaging system controller computer 101 is selectively couplable to the sensor electronic processor 117 and/or the interface microcontroller 121 by a wired or wireless connection including, for example, a USB cable or a Wi-Fi connection.

The image sensor housing 109 also includes a multi-dimensional sensor 123 providing information about the placement, movement, and operation of the imaging sensor 108. In the example of FIG. 1A, the multi-dimensional sensor 123 includes a three-dimensional accelerometer 125 configured to output a signal indicative of a magnitude and direction of acceleration in three-dimensional space. The multi-dimensional sensor 123 also includes a three-dimensional gyroscopic sensor 127 and a three-dimensional magnetometer 129.

In various implementations, the imaging sensor 108 may also include additional sensor components. In the particular example of FIG. 1A, the multi-dimensional sensor 123 includes a temperature sensor 131 configured to output a signal indicative of a temperature of the imaging sensor 108. The imaging sensor 108 also includes a current/voltage monitor circuit 133 configured to output a signal indicative of a current and/or a voltage of the supplied power provided to the imaging sensor 108. The imaging sensor 108 also includes an air pressure sensor 135 configured to output a signal indicative of an air pressure within the imaging sensor 108. In some implementations, the current/voltage monitor circuit 133 is not positioned within the imaging sensor housing 109 and instead is provided in a separate housing that is externally coupled to the imaging sensor housing 109.

In the example of FIG. 1A, the current/voltage monitor circuit 133 and the air pressure sensor 135 are provided as separate components and are not integrated into the multi-dimensional sensor 123. However, in other implementations, the current/voltage monitor circuit 133, the air pressure sensor 135, and the temperature sensor 131 may be integrated into the multi-dimensional sensor 123. Conversely, in some implementations, the accelerometer 125, the gyroscopic sensor 127, the magnetometer 129, the temperature sensor 131, the current/voltage monitor circuit 133, and the air pressure sensor 135 are all provided within the imaging sensor housing 109 as separate components without any single internal structure or housing identifiable as a "multi-dimensional sensor." In those implementations, the multi-dimensional sensor 123 refers collectively to one or more sensor components provided within the imaging sensor housing 109. Lastly, although the example of FIG. 1A presents a specific list of types of sensor components within the imaging sensor housing 109, in other implementations, the imaging sensor 108 may include more, fewer, or different sensor components.

In the imaging system 100 illustrated in FIG. 1A, the imaging system controller computer 101 monitors the outputs from the sensors positioned within the imaging sensor housing 109 and operates the various components based at least in part on the outputs from the sensors. In particular, as described in greater detail below, the imaging system controller computer 101 operates the imaging sensor 108 in one of a plurality of different operating states and transitions between the operating states based at least in part on outputs from the sensors of the imaging sensor 108. In some implementations, the plurality of different operating states includes one or more "low power" states, one or more "ready" states, and one or more "armed" states.

When operating in a "low power" state, electrical power provided to the imaging sensor 108 and/or the electrical power consumed by various components of the imaging sensor 108 is reduced and some functions/operations of the imaging sensor 108 are prohibited or restricted (barring a manual override). For example, in some implementations, the imaging sensor 108—particularly the image sensor array 115—cannot be armed when the imaging sensor 108 is operated in the "low power" state. Instead, the imaging sensor 108 must first transition to a "ready" state in response to a determination that a first state transition criteria has been satisfied. When operating in the "ready" state, the imaging sensor 108 is not yet armed, but can be transitioned into the "armed" operating state in response to an input or a condition detected by the imaging system controller computer 101 indicating that a second state transition criteria has been satisfied. In some implementations, electrical power provided to one or more of the sensor components in the imaging sensor housing 109 is also reduced or disconnected while the imaging sensor 108 is operating in the "low power" state.

In some implementations, the communication interface between the imaging sensor 108 and the imaging system controller computer 101 is disabled when the imaging sensor 108 is operating in the "low power" state. For example, in the system of FIG. 1A, the interface microcontroller 121 may be turned off or powered down when the imaging sensor 108 enters the "low power" state. Alternatively, in some implementations, the interface microcontroller 121 is itself configured to adjust how it controls the connection between the imaging system controller computer 101 and the interface microcontroller 121 based on whether the imaging sensor 108 is operating in the "low power" state.

In the example of FIG. 1A, the sensor electronic processor 117 monitors the output of the various sensor components and may be triggered to initiate an "interrupt" routine and/or output an "interrupt" flag in response to detecting that a state transition criteria has been satisfied as described in further detail below. In this example, the interface microcontroller 121 resumes operation in response to the interrupt flag output by the sensor electronic processor 117 and communication between the imaging sensor 108 and the imaging sensor controller computer 101 is restored. Accordingly, although several of the examples presented below discuss functionality performed and executed by the electronic processor 103 of the imaging system controller computer 101, in other implementations, this functionality (including the detection of state transition criteria and the transitions between operating state) is provided in full or in part by another electronic processor—for example, the sensor electronic processor 117.

FIG. 1A generally illustrates the control logic within the imaging sensor 108 as a sensor electronic processor 117 (that both receives captured image data from the image sensor array 115 and monitors the outputs of the other sensor components within the imaging sensor 108) and an interface microcontroller 121 (that controls communication between the imaging sensor 108 and the imaging system controller computer 101). However, this control functionality may be implemented using one or more other processing devices. For example, in some implementations the functionality described in reference to the sensor electronic processor 117 and the interface microcontroller 121 is provided by a single microcontroller component positioned within the imaging sensor housing. Conversely, in other implementations, the functionality described in reference to the sensor electronic processor 117 is distributed across two or more controllers positioned within the image sensor housing 109 and/or within the multi-dimensional sensor 123.

Figure 1B:
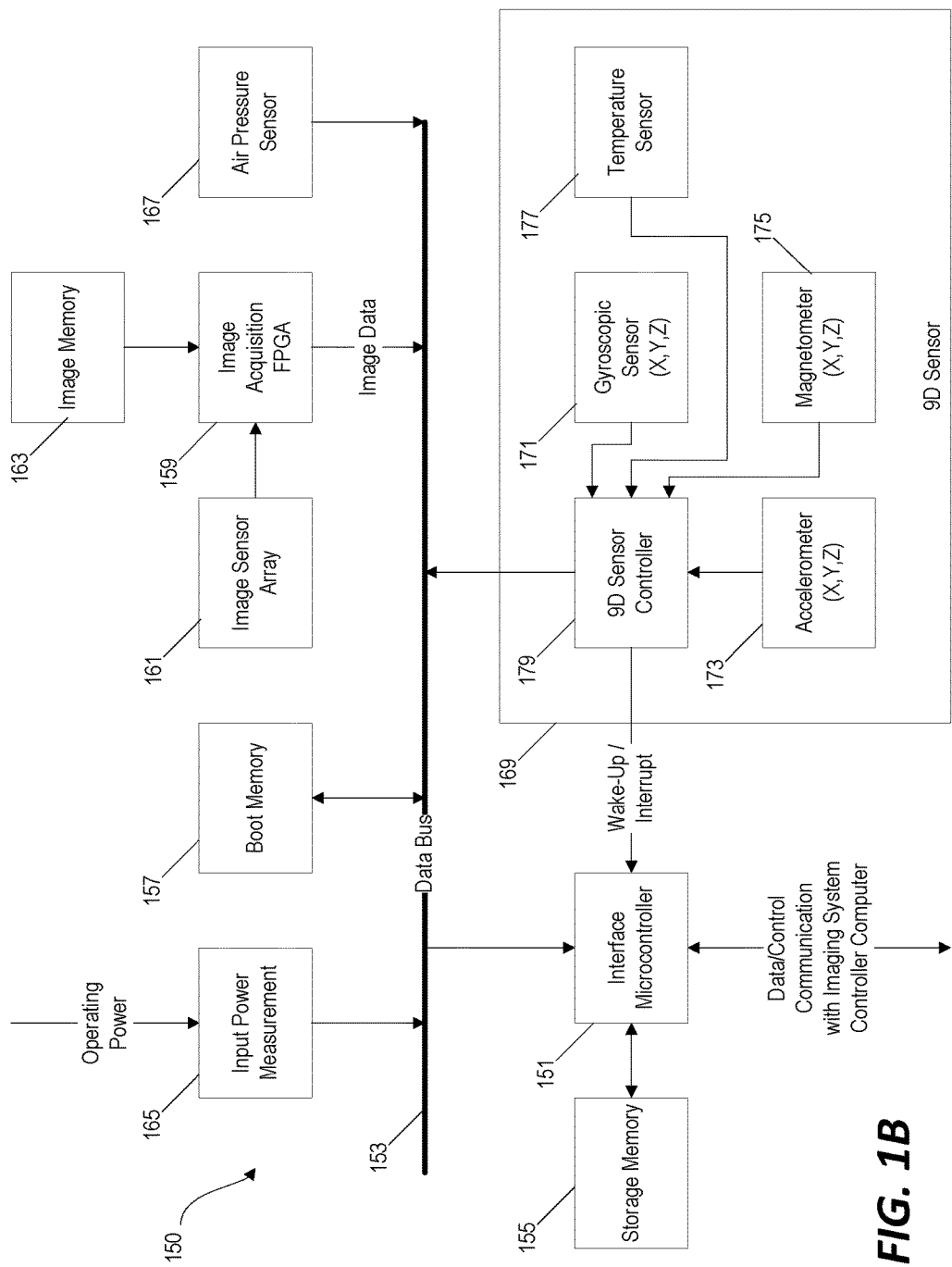
FIG. 1B is a block diagram of an imaging sensor for use in the imaging system of FIG. 1A with a three-controller logic architecture.

FIG. 1B illustrates an example of an imaging sensor 150 that includes three separate controllers. The first controller is an interface microcontroller 151 that is communicatively coupled to a data bus 153 and is configured to manage communications between the imaging sensor 150 and the imaging system controller computer (not pictured). In some implementations, the interface controller 151 is a USB controller and is configured to provide communications between the imaging sensor 150 and an external computer system through a wired USB cable interface. The interface controller 151 is directly coupled to a storage memory 155 and is coupled to a boot memory 157 through the data bus 153.

The second controller in the example of FIG. 1B is an image acquisition field programmable gate array (FPGA) 159. The image acquisition FPGA 159 is directly coupled to the image sensor array 161 (or other image sensing component). Image data captured by the image sensor array 161 is streamed via the image acquisition FPGA 159 to an image memory 163. In this example, the image memory 163 includes an SRAM device. The image acquisition FPGA 159 is configured to handle image data transfer between the image sensor array 161, the image memory 163, and the interface microcontroller 151. In some implementations, the image acquisition FPGA is also configured to implement various control and monitoring functions for the image sensor array 161 including, for example, a dose sensing algorithm.

Various other sensor components are also coupled to the data bus 153 in the example of FIG. 1B. An input power measurement circuit 165 is configured to monitor the voltage and current operating power provided to the imaging sensor 150 and to output a signal indicative of the measured voltage and current to the data bus 153. An air pressure sensor 167 is positioned within a housing of the imaging sensor 150 and coupled to provide an output signal to the data bus 153. In some implementations, the air pressure sensor 167 is configured to measure an absolute air pressure value and output the measured value to the data bus 153 while, in other implementations, the air pressure sensor 167 is configured to output a signal to the data bus 153 indicative of a change in the internal air pressure and/or to output an air pressure interrupt flag to the data bus 153 in response to detecting a change in air pressure that exceeds a threshold.

In the example of FIG. 1B, a nine-dimensional (9D) sensor 169 is also communicatively coupled to the data bus 153. Like the multi-dimensional sensor 123 in the example of FIG. 1A, the 9D sensor 169 includes a three-dimensional gyroscopic sensor 171, a three-dimensional accelerometer 173, and a three-dimensional magnetometer 175 providing measurement data indicative of nine dimensions of movement, position, and orientation of the imaging sensor 150. The 9D sensor 169 also includes a temperature sensor 177.

The third controller in the example of FIG. 1B is a 9D sensor controller 179 positioned within the 9D sensor 169. The 9D sensor controller 179 is configured to monitor and control the various sensor components of the 9D sensor 169 and to output data/signals to the data bus 153 indicative of the conditions and parameters measured by the sensor components. The 9D sensor controller 179 also includes one or more dedicated "interrupt" pins coupled directly to the interface microcontroller 151. In some implementations, the 9D sensor controller 179 is configured to monitor the outputs from one or more of the sensor components of the 9D sensor 169, to determine whether certain state transition criteria is satisfied, and to output an "interrupt" flag signal to the interface microcontroller 151 in response to determining that the state transition criteria has been satisfied. This "interrupt" flag signal output by the 9D sensor controller 179 to the interface microcontroller 151 can, in some implementations, cause the interface microcontroller 151 to transition from one operating state to another (for example, a transition from the "low power" state to a "ready" state as discussed above).

Accordingly, although certain examples presented in this disclosure refer generally to determinations made by or functionality provided by the sensor electronic processor 117, in various other implementations, this functionality can be implemented by one or more different controller components internal to the imaging sensor 108/150 or, in some cases, within the imaging system controller computer 101 depending on the particular control logic architecture that is implemented. For example, an "interrupt routine" may refer to a sub-routine or functionality provided in response to a detected condition. An "interrupt signal" or "interrupt flag" refers to an output (for example, a binary output) from one controller or sensor that, when received by another logic component, causes the component to perform or modify the functionality of the system (for example, initiating execution of an "interrupt routine").

In some implementations, before transitioning from the "low power" state into the "ready" state or, in other implementations, before transitioning from the "ready" state into the "armed" state, the imaging system controller computer 101 or the sensor electronic processor 117 implements an error condition check routine to ensure that the imaging sensor 108 is operating properly. In other implementations, an error condition check routine is performed periodically while the imaging sensor 108 is operated in a single operating state—for example, after each image is captured while operating in the "armed" state. In still other implementations, an error notification can cause the electronic processor to automatically launch other system check routines or automated self-correction routines. In the discussion below, functionality or steps that are described as being performed by the "imaging system" are implemented, in various embodiments, by one or more of the controllers of the imaging system including, for example, the sensor electronic processor 117, the interface microcontroller 121, the electronic processor 103 of the imaging system controller computer 101, or the 9D sensor controller 179 of the 9D sensor 169.

An example error condition check routine is illustrated in FIGS. 2A through 2E. Beginning in FIG. 2A, after the error condition check routine is initiated (block 201), the imaging system 100 first performs a "voltage" check (block 203). If the imaging sensor 108 passes the voltage check, the imaging system 100 performs a "current" check (block 205). If the imaging sensor 108 passes the current check, then the imaging system 100 performs a "temperature" check (block 207). If the imaging sensor 108 passes the temperature check, then the imaging system 100 perform an "acceleration" check (block 209). If the imaging sensor 108 passes each of the error condition check routines, then the imaging system 100 continues with the operation of the imaging sensor 108 (for example, continuing to operate in the "armed" state or transition into the "armed" state).

FIG. 2B illustrates an example of the "voltage check" routine in greater detail. Based on an output from the current/voltage monitor circuit 133, the imaging system 100 determines a voltage of the electrical power provided to the imaging sensor 108, for example, through the USB cable coupled to the imaging system controller computer 101 (block 211). If the detected voltage does not exceeds a first voltage threshold (V1) (block 213), then the imaging system 100 determines that there is an error condition either within the imaging sensor 108 or the cable connecting the imaging sensor 108 to its power source. In response to this detected condition, the imaging system 100 disarms the sensor and, in some implementations, prevents the sensor from transitioning into the "armed" state (block 215). A "low voltage" notice is output to the user (block 217). The "low voltage" notice can be output, for example, as a graphical notice shown on a display coupled to the imaging system controller computer 101. The "low voltage" notice, in some implementations, displays a value of the detected voltage and instructs the user on possible corrective measures. For example, the "low voltage" notice may instruct the user to try connecting the imaging sensor 108 to another USB port, connecting the imaging sensor 108 to a different computer/imaging system controller computer 101, or connecting the imaging sensor 108 to the imaging system controller computer 101 using a different USB cable. The "low voltage" notice may also instruct the user to contact technical support if the condition persists. In some implementations, detected error/fault conditions (for example, the "low voltage" condition and other conditions described below) are recorded to a log file used to track errors/faults of an imaging sensor 108.

Similarly, if the imaging system 100 determines that the detected voltage exceeds a second voltage threshold (V2) that is higher than the first voltage threshold (block 219), then the imaging system 100 detects a "high voltage" condition on the imaging sensor 108. The imaging system 100 either disarms the sensor and, in some implementations, prevents the sensor from transitioning into the "armed" state (block 221). A "high voltage" notice is output to the user (block 223). Because a "high voltage" condition can potentially damage the imaging sensor 108 hardware, the "high voltage" notice instructs the user to promptly unplug the imaging sensor 108 from the power supply to prevent damage. In some implementations, based on information including, for example, the magnitude of the detected voltage, the "high voltage" notice includes user instructions informing the user to try connecting the imaging sensor 108 to a different computer or to contact technical support. In still other implementations, the imaging system 100 may be configured to transmit an error message directly to a technical support system and to include in the error message an identification and location of the imaging system controller computer 101 that detected the error condition and an indication of the magnitude of the detected voltage.

If, however, the detected voltage of the electrical power provided to the imaging sensor 108 is between the first voltage threshold and the second voltage threshold, then then imaging sensor 108 has passed the "voltage check" portion of the test. The imaging system 100 then continues to the "current check" routine (block 225).

Figure 2C:
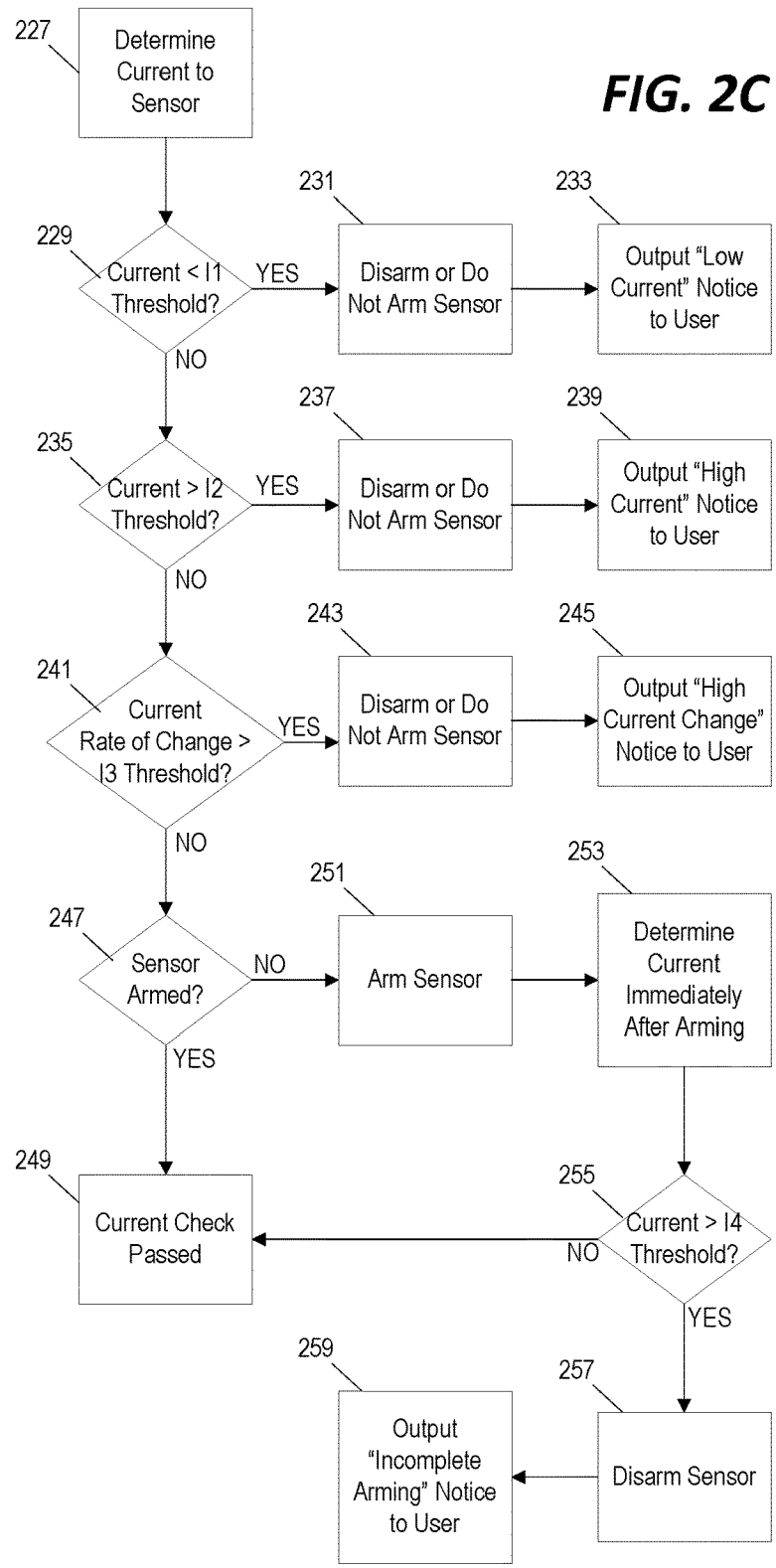
FIG. 2C is a flowchart of a method for checking the sensor current in the method of FIG. 2A.
Figure 2E:
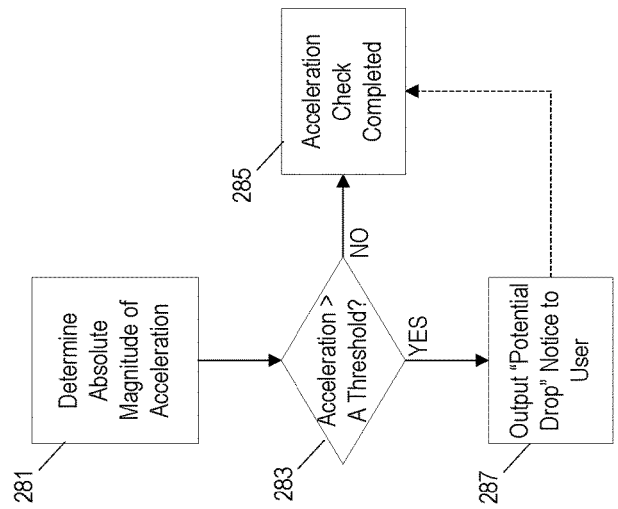
FIG. 2E is a flowchart of a method for detecting a potential dropped sensor (or when a sensor is dropped) in the method of FIG. 2A.
Figure 2D:
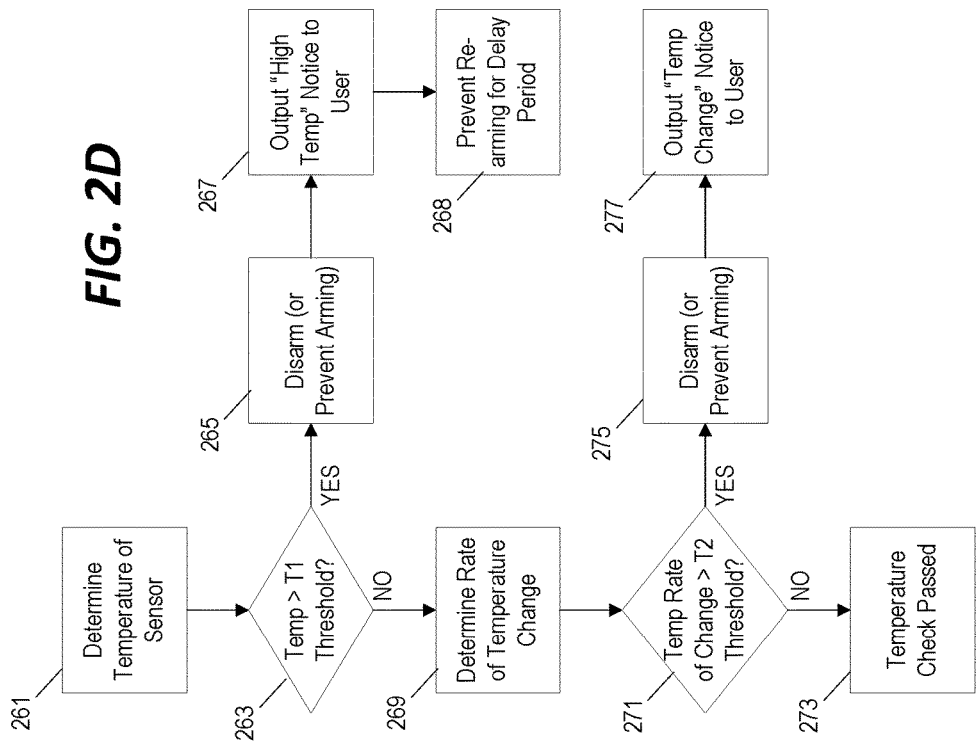
FIG. 2D is a flowchart of a method for checking the sensor temperature in the method of FIG. 2A.

FIG. 2C illustrates the "current check" component (block 205 of FIG. 2A) of the error condition check routine. In some implementations, if the imaging sensor 108 does not pass the "voltage check" component (block 203 of FIG. 2A), then the imaging system 100 disarms the imaging sensor 108 without performing the current check component. However, after passing the "voltage check" component, the imaging system 100 begins the current check component by determining the current of the electrical power provided to the imaging sensor 108 (block 227). If the current is below a first current threshold (I1) (block 229), then the imaging system 100 determines that a "low current" condition exists and, in response, the imaging sensor 108 is disarmed or prohibited from arming (block 231) and a "low current" notice is output on the graphical user interface of the imaging system controller computer 101 (block 233). The "low current" notice may include a magnitude of the determined current, an instruction for troubleshooting the detected problem (for example, try another USB port, another computer, or another USB cable), or an instruction to contact technical support.

If the current is above the first current threshold (I1), then the imaging system 100 determines whether the detected current is above a second current threshold (I2) that is greater than the first current threshold (block 235). If so, the imaging system 100 determines that a "high current" condition exists and, in response, disarms the imaging sensor 108 and, in some implementations, prevents the imaging sensor 108 from arming (block 237). A "high current" notice is output to the user (block 239). Because a high current can potentially damage the hardware of the imaging sensor 108, in some implementations, the "high current" notice instructs the user to disconnect the sensor immediately to prevent damage. The "high current" notice may also instruct the user to try connecting the imaging sensor 108 to another computer (for example, imaging system controller computer 101), to connect using another cable, or to contact technical support.

If the detected current is between the first current threshold and the second current threshold, the imaging system 100 then determines a rate of change of the detected current. The rate of change of the detected current is determined based on the most recently detected current and one or more previously detected currents. In some implementations, a current log file is maintained so that the rate of change of the detected current can be tracked over longer periods of time by extracting or reading data from the log file. The rate of change of the current is compared to a rate of change current threshold (I3) (block 241). In some implementations, this comparison indicates whether the current has increased by more than the defined threshold with respect to a baseline current determined at the time that the imaging sensor 108 was plugged into the power source (for example, the imaging system controller computer 101). If the rate of change exceeds the rate of change current threshold, the imaging sensor 108 is disarmed or, in some implementations, is prevented from arming (block 243). A "high current change" notice is output to the user on the graphical user interface of the imaging system controller computer 101 (block 245). The "high current change" notice instructs the user to disconnect the imaging sensor 108 in order to prevent damage and, in some implementations, provides further instructions for troubleshooting/mitigation including, for example, contacting technical support.

If the imaging sensor 108 passes all three of these checks and the sensor is already armed (block 247), then the imaging system 100 continues to operate the imaging sensor 108 in its current operating state or continues to the other components of the error condition check routine (block 249). However, if the imaging sensor 108 is not yet armed (at block 247), then the current check component includes another verification test. The imaging system 100 arms the imaging sensor 108 (block 251) and measures the current immediately after arming the imaging sensor 108 (block 253). If the current detected immediately after arming the imaging sensor 108 exceeds a fourth current threshold (I4) (block 255), then the imaging sensor 108 is disarmed (block 257) and an "incomplete arming" notice is output to the user indicating that an error condition was detected based on the detected electrical current during the arming process (block 259). The "incomplete arming" notice indicates to the user that the imaging sensor 108 was not successfully armed and that x-ray images will not be captured. In some implementations, the "incomplete arming" notice may also provide additional instructions for mitigating/troubleshooting the error condition including, for example, trying another USB port, computer, or USB cable or contacting technical support.

However, if the current detected immediately after arming the imaging sensor 108 is below the fourth current threshold (I4) (block 255), then the imaging system 100 proceeds with operating the imaging sensor 108 in the "armed" state and/or proceeds to the next test in the error condition check routine. In the example of FIGS. 2A through 2E, an imaging sensor 108 that is transitioning from the "ready" state to the "armed" state becomes "armed" during the current check mechanism and remains armed for the "temperature" check component (block 207 in FIG. 2A) and the acceleration check (block 209 in FIG. 2A). However, in some other implementations, the portion of the current check component that compares the detected current immediately after the imaging sensor 108 is armed to a fourth current threshold (I4) (block 255) is delayed until after one or more additional tests are performed while the imaging sensor 108 is unarmed.

After completing the voltage check component (block 203 in FIG. 2A) and the current check component (block 205 in FIG. 2A), the imaging system 100 applies a temperature check to the imaging sensor 108. In this example, the temperature check is applied after the imaging sensor 108 has been armed. However, in other implementations, the imaging system 100 performs the temperature check before arming the imaging sensor 108. If the imaging sensor 108 passes the voltage check and the current check components, then an abnormal temperature detected during the temperature check may indicate a problem with both the current of the imaging sensor 108 and the voltage/current monitor circuit 133.

In performing the temperature check component, the imaging system 100 first determines a temperature of the sensor (block 261) and then compares the detected temperature to a first temperature threshold (T1) (block 263). If the detected temperature exceeds the first temperature threshold, then the imaging system 100 determines that an error condition exists, disarms the imaging sensor 108 (or, in some implementations, prevents the imaging sensor 108 from arming) (block 265) and outputs a "high temperature" notice to the user on the graphical user interface of the imaging system controller computer 101 (block 267). Because a high temperature may be indicative of a high current or an electrical short in the circuitry of the imaging sensor 108, the "high temperature" notice in some implementations instructs the user to immediately disconnect the imaging sensor 108 from the power source (for example, the imaging system controller computer 101) and to contact technical support. In some implementations, the imaging system 100 then continues to prevent the imaging sensor 108 from being re-armed for a defined delay period to allow the imaging sensor 108 to cool (block 268).

If the temperature of the imaging sensor 108 is below the first temperature threshold (T1), the imaging system 100 then considers whether there is an abnormal rate of temperature change in the imaging sensor 108. The imaging system 100 determines a rate of temperature change (block 269) based on the most recently detected temperature and one or more earlier detected temperatures and compares the calculated rate of temperature change to a temperature change threshold (T2) (block 271). If the rate of temperature change is below the temperature change threshold, then the imaging sensor 108 has passed the temperature component of the error condition check routine and the imaging system 100 continues to operate the imaging sensor 108 (block 273). However, if the rate of temperature change exceeds the threshold, the imaging system 100 disarms the imaging sensor 108 (or prevents arming of the imaging sensor 108) (block 273) and outputs a "temperature change" notice to the user on the graphical user interface of the imaging system controller computer 101 (block 277). The "temperature change" notice may instruct the user to immediately disconnect the imaging sensor 108 to prevent damage and may also instruct the user to contact technical support.

Lastly, if the imaging sensor 108 has passed the voltage component, the current component, and the temperature component of the error condition check routine, then the imaging system 100 evaluates the output of the accelerometer 127 to determine whether the imaging sensor 108 has been dropped during or prior to the arming process. The imaging system 100 determines an absolute magnitude of acceleration based on the output of the accelerometer 125 (block 281). In some implementations, the imaging system 100 determines a maximum acceleration detected since the imaging sensor 108 transitioned from the "low power" state into the "ready" state or since the last "acceleration check" was performed. If the detected acceleration is less than the acceleration threshold (block 283), then the imaging sensor 108 is armed and continues its normal operation (block 285). However, if the detected acceleration exceeds an acceleration threshold indicative of a sudden drop or other potentially damaging impact, then an "potential damage" notice is output to the user on the graphical user interface of the imaging system controller computer 101 (block 287). The "potential damage" notice indicates that a potentially damaging event was detected and instructs the user to visually inspect the imaging sensor housing 109 for visible damage. In some implementations, the imaging sensor 108 continues to operate in the "armed" state even after a potential damage" event is detected as long as the other components of the error condition check routine have passed successfully. Furthermore, as noted above, in some implementations, the determination of whether the output of the accelerometer exceeds the acceleration threshold indicative of a sudden drop is performed by a logic component positioned within the imaging sensor housing 109 and configured to output an interrupt in response—this enables the acceleration indicative of a "drop" event to be detected quickly without the need for communication between the imaging sensor 108 and the imaging system controller computer 101 and further processing by the imaging system controller computer 101. In some embodiments, this logic component is provided as the sensor electronic processor 117 (of FIG. 1A), the 9D sensor controller 179 (of FIG. 1B), or another logic circuit.

The example discussed above in reference to FIGS. 2A through 2E is just one example of an error condition check routine that is applied to an imaging sensor 108. In other implementations, the steps may be performed in another order and may include more, fewer, or alternative tests and steps. In addition, although most of the failed tests discussed above result only in a notice displayed to the user on the graphical user interface of the imaging system controller computer 101, other implementations may provide automated mitigation steps. For example, the imaging system 100 may be configured to automatically disconnect the imaging sensor 108 from the power source if one or more specific tests are not passed. Additionally, instead of instructing a user to contact technical support if a problem persists, the imaging system 100 may be configured to automatically transmit a message to a technical support system including an identification and/or location of the imaging system controller computer 101. The message may also include other details about the failed test (including the sensor output reading that caused the imaging sensor 108 to fail the test).

Figure 3A:
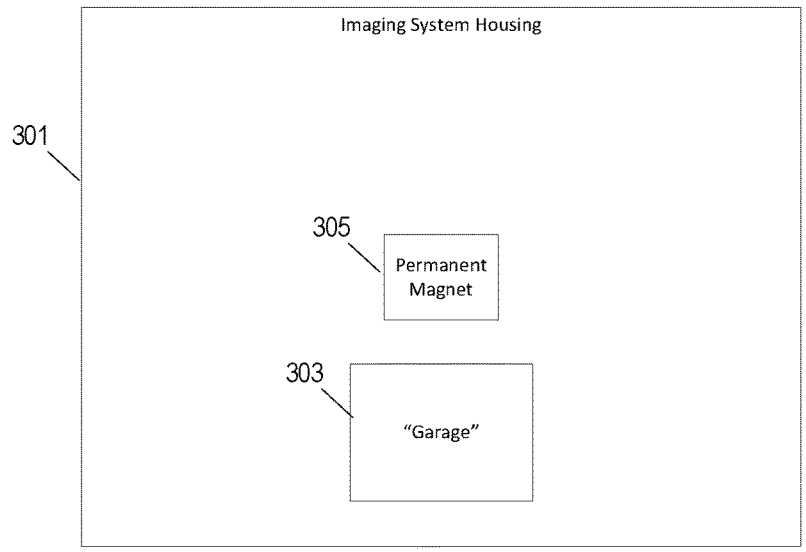
FIG. 3A is a partially transparent elevation view of a storage compartment (sometimes referred to as a "garage") for the imaging sensor in the imaging system of FIG. 1A.
Figure 3B:
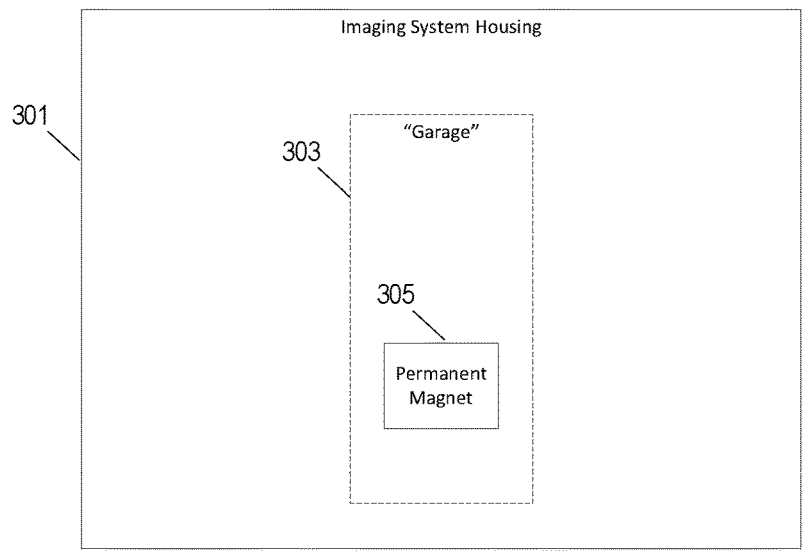
FIG. 3B is a partially transparent overhead view of the storage compartment of FIG. 3A.

As discussed above, one or more of the error condition check routines illustrated in FIGS. 2A through 2E above may be performed periodically while an imaging sensor 108 is operated in an "armed" state or may be performed as the imaging sensor 108 is transitioned from one state to another. However, the imaging system 100 may be configured to use the output from the various sensor components of the imaging sensor 108 to transition from one operating state to another. For example, FIGS. 3A and 3B illustrate an imaging system housing 301 that includes a "garage" 303 or "storage holder" for storage of the imaging sensor 108 when it is not in use. A permanent magnet 305 is integrated into the imaging system housing 301 and positioned to apply a magnetic field to the imaging sensor 108 when it is stored in the "garage" 303. The magnetic field generated by the permanent magnet 305 has a magnitude and vector direction that can be detected and identified based on the output of the magnetometer 129 of the imaging sensor 108.

Figure 4:
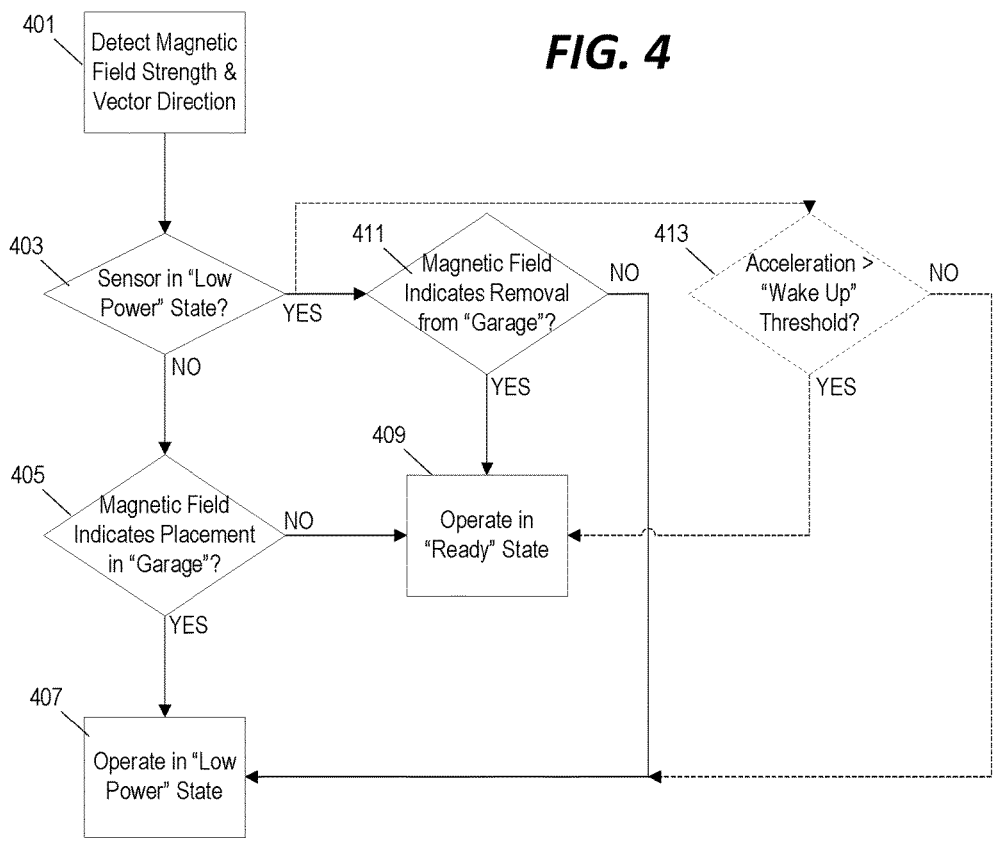
FIG. 4 is a flowchart of a method for transitioning between operating states of the imaging system of FIG. 1A based on whether the sensor is detected in the storage compartment of FIGS. 3A and 3B.

As illustrated in FIG. 4, the imaging system 100 is configured to transition between the "low power" state and the "ready" state based on whether the output of the magnetometer 129 indicates that the imaging sensor 108 is positioned within the garage 303 of the imaging system housing 301. The imaging system 100 periodically processes the output signal from the magnetometer 129 to detect a strength and vector direction of a magnetic field relative to the imaging sensor 108 (block 401). If the imaging sensor 108 is not currently operating in a "low power" state (block 403), then the detected magnetic field is analyzed to determine whether the detected magnetic field is indicative of placement of the imaging sensor 108 in the "garage" 303 or storage holder (block 405). If a magnetic field indicative of placement in the "garage" 303 is detected, then the imaging sensor 108 is transitioned into the "low power" state (block 407). However, if the magnetic field indicative of placement in the "garage" 303 is not detected, then the imaging sensor 108 remains in the "ready" state (block 409).

When the imaging sensor 108 is already operating in the "low power" mode (block 403), the imaging system 100 determines whether the detected magnetic field is indicative of removal of the imaging sensor 108 from the "garage" 303 (block 411). In some embodiments, a magnetic field indicative of removal of the imaging sensor 108 from the "garage" 303 is one in which the magnitude of the detected magnetic field drops below a defined threshold and/or the vector direction of the detected magnetic field deviates from the vector direction of the magnetic field expected to be applied by the permanent magnet 305 by a predetermined amount. If a magnetic field indicative of removal of the imaging sensor 108 from the "garage" 303 is detected (block 411), then the imaging sensor 108 is transitioned from the "low power" mode into the "ready" mode (block 409). However, if the detected magnetic field continues to indicate that the imaging sensor 108 is placed within the "garage" 303, then the imaging sensor 108 remains in the "low power" state (block 407).

In some implementations, the imaging sensor 108 "wakes up" (for example, transitions from the "low power" state into the "ready" state) based only on a detected change in the magnetic field applied by the permanent magnet 305. However, in some implementations, additional or alternative information provided by the sensor components of the imaging sensor 108 are used to determine whether to transition the imaging sensor 108 into the "ready" mode. For example, as also illustrated in FIG. 4, while the imaging sensor 108 is operating in the "low power" state, the imaging system 100 may be configured to periodically detect the acceleration of the imaging sensor 108 based on the output of the accelerometer 125. If the detected acceleration exceeds a "wake up" threshold (block 413), the imaging sensor 108 is transitioned into the "ready" state (block 409) and, if the detected acceleration is below the "wake up" threshold, the imaging sensor 108 remains in the "low power" state (block 407). As illustrated in the example of FIG. 4, the magnetic field and acceleration "wake up" criteria are applied in parallel in some embodiments and a condition meeting either criterion will cause the imaging sensor 108 to transition into the "ready" state. However, in other implementations, the magnetic field and acceleration "wake up" criteria are applied in series and both criteria must be satisfied before the imaging sensor 108 will be transitioned into the "ready" state.

As discussed above, in some implementations, the determinations described in reference to FIG. 4 are performed by the imaging system controller computer 101 based on data received from the imaging sensor 108. However, in other implementations—for example, in implementations where communication between the imaging sensor 108 and the imaging system controller computer 101 are disabled while the imaging sensor 108 is operated in the low power mode—some or all of the state transition determinations are made by a logic component included within the imaging sensor 108 (for example, the sensor electronic processor 117 in the example of FIG. 1A). In still other implementations, one logic component positioned within the imaging sensor housing 109 and/or the multi-dimensional sensor 123 (for example, the 9D sensor controller 179 in the example of FIG. 1B) is configured to generate an "interrupt" flag in response to certain measured conditions. For example, in reference to the method of FIG. 4, the 9D sensor controller 179 of FIG. 1B may be configured to generate an interrupt flag when the output of the accelerometer 173 indicates that the acceleration of the imaging sensor 150 exceeds the "wake up" threshold. This interrupt flag causes the imaging sensor 150 to transition from the low power state into the ready state, in part, by the interface microcontroller 151 restoring communication between the imaging sensor 150 and the imaging system controller computer 101. When the state transition condition is initiated by an interrupt (as in the example of FIG. 1B), the imaging sensor 150 may not need to communicate acceleration data to the imaging system controller computer 101 as frequently as might be required if the imaging system controller computer 101 were periodically monitoring the acceleration of the imaging sensor 108 to determine whether the "wake up" threshold is exceeded. In some implementations, no acceleration data is communicated from the imaging sensor 108 to the imaging system controller computer 101 while the imaging sensor 108 is operating in the low power state.

Figure 3C:
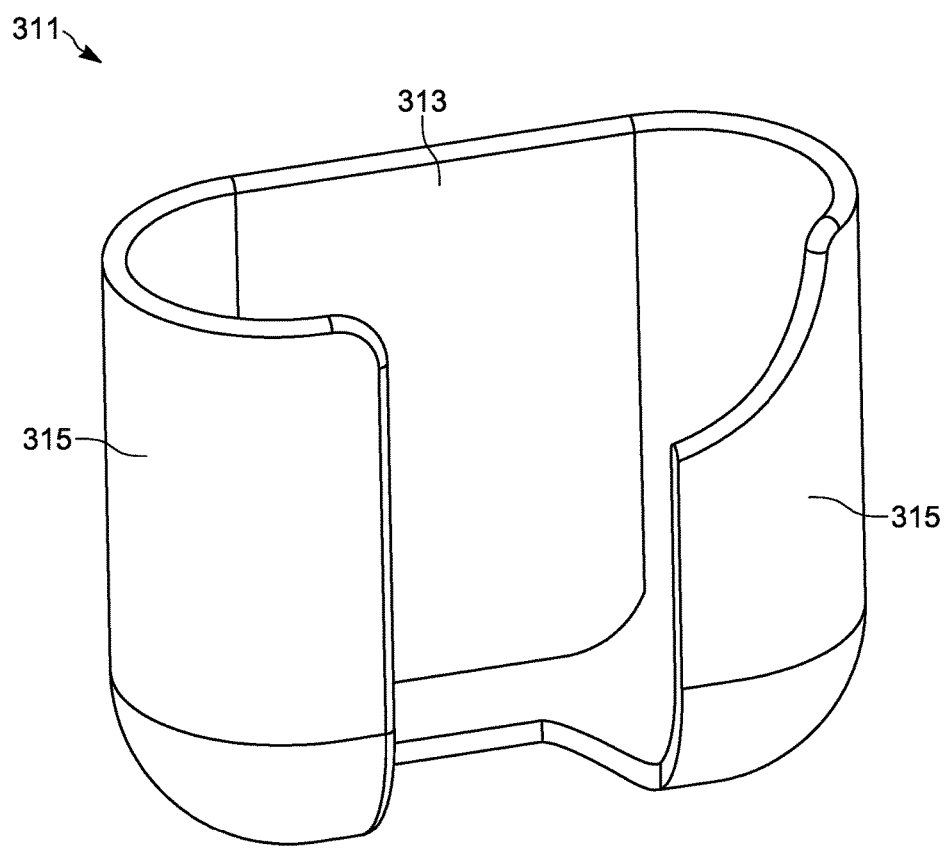
FIG. 3C is a perspective view of an alternative example of an imaging sensor storage without an imaging sensor.
Figure 3D:
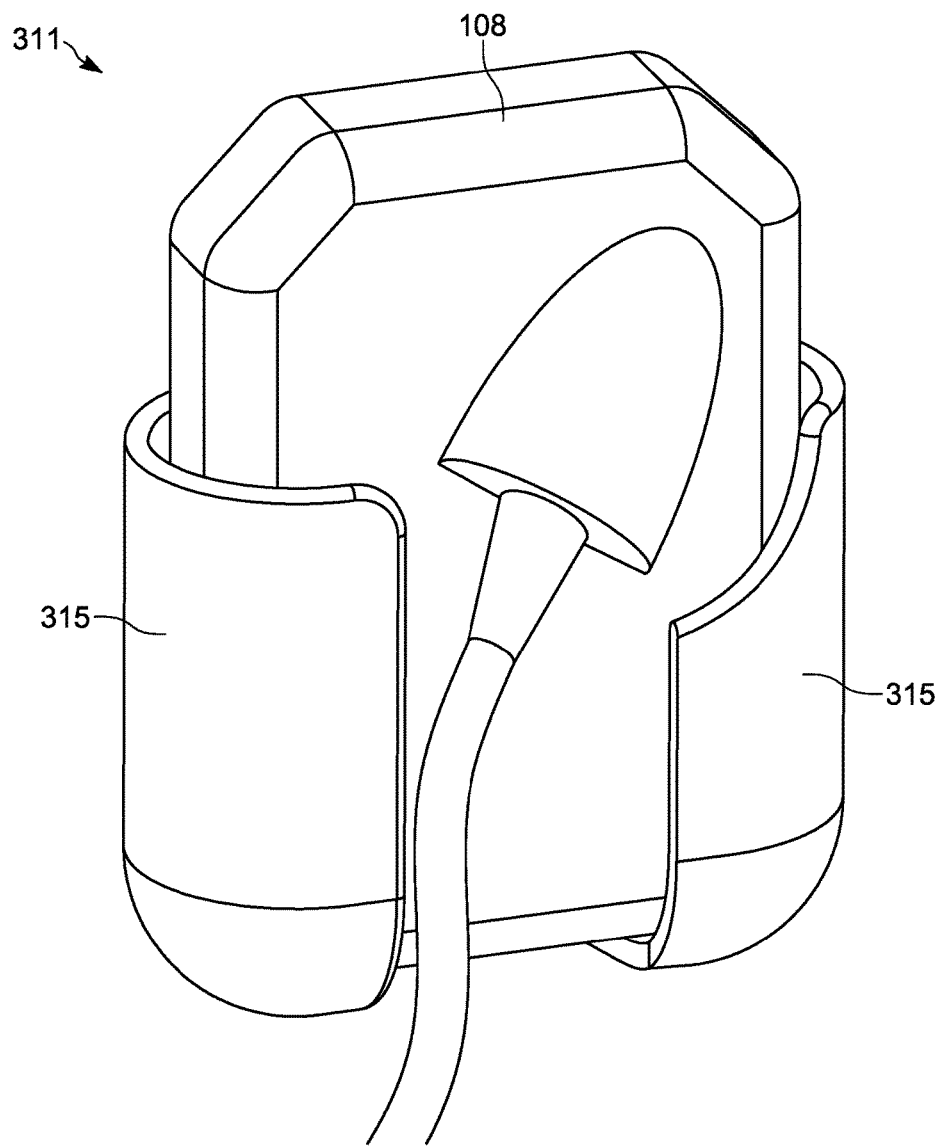
FIG. 3D is a perspective view of the alternative example of the imaging sensor storage of FIG. 3C with an imaging sensor therein.

In the example of FIGS. 3A and 3B, the permanent magnet 305 is positioned above the "garage" 303 or permanently integrated into a wall or surface of the garage. However, in other implementations, the permanent magnet 305 can be positioned at other locations to provide a unique and detectable magnetic field when an imaging sensor 108 is positioned within the "garage" 303. Similarly, although the storage holder is illustrated in FIGS. 3A and 3B as a "garage," the storage holder can be provided in other configurations in other implementation including, for example, as a "holster" or a clip positioned on the side of the imaging system housing 301. In still other implementations, the storage holder or "garage" 303 may be provided as a housing that is completely separate from the imaging system controller computer 101 and may be positionable near the workspace of the dental practitioner for easy access. For example, FIGS. 3C and 3D illustrate an example of an image sensor storage 311 where the imaging sensor 108 is supported against a backplate 313 and by a pair of support arms 315. In this example, the permanent magnet is incorporated into the backplate 313 to generate a magnetic field and the imaging sensor 108 is not fully enclosed when placed in the image sensor storage 311. FIG. 3C shows only the image sensor storage 311 and FIG. 3D shows the image sensor storage 311 with the imaging sensor 108 positioned therein.

Although the example of FIGS. 3A and 3B discuss using a permanent magnet to detect whether the imaging sensor 108 is placed in the "garage" 303 and, based on that determination, transition between operating states, in some other implementations, other mechanisms may be used to detect whether the imaging sensor 108 is in a storage position and to transition between operating states accordingly.

In still other implementations, the magnetometer 129 may be disabled when the imaging sensor 108 is operating in the "low power" state. Therefore, the determination of when to transition the imaging sensor 108 into the "ready" state is based on criteria from another sensor or sensors—for example, the acceleration criteria (block 413) may be applied as the only test to determine when to transition the device from the "low power" state into the "ready" state.

Figure 5:
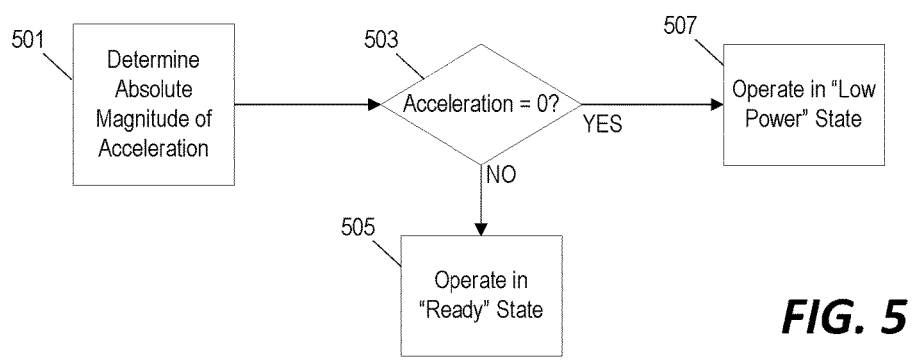
FIG. 5 is a flowchart of a method for transitioning between operating states of the imaging sensor of FIG. 1A or FIG. 1B based on an acceleration detected by the multi-dimensional sensor of the imaging sensor.

Similarly, in some implementations, acceleration as detected based on the output from the accelerometer 125 may govern the transition between the "ready" state and the "low power" state even without a determination that the imaging sensor 108 has been placed in the "garage" 303. This may occur, for example, when a dental practitioner places the imaging sensor 108 on a counter or table. As illustrated in FIG. 5, the imaging system 100 determines an absolute magnitude of acceleration based on the output from the accelerometer 125 (block 501). If the detected acceleration does not equal zero (indicating that the device is moving) (block 503), then the imaging sensor 108 is operated in the "ready" state. Conversely, if the detected acceleration indicates that the imaging sensor 108 is stationary (block 503), then the imaging sensor 108 is placed in the "low power" state (block 507).

In some implementations, the imaging sensor 108 is not transitioned from the "ready" state into the "low power" state immediately upon detection of an acceleration equal to zero and, instead, the zero acceleration must be detected continuously for a defined period of time before the imaging sensor 108 is transitioned into the "low power" state based on the criteria of FIG. 5. In other implementations, the state transition criteria described in reference to FIG. 5 is not applied if the imaging sensor 108 is operating in the "armed" state and the imaging sensor 108 must first be operating in the "ready" state before the imaging sensor 108 can transition into the "low power" state based on a detected acceleration of zero.

State transitions may also be governed by detecting and identifying other magnetic fields acting upon the imaging sensor 108. For example, FIGS. 6A and 6B each shows a sensor positioner configured to hold the imaging sensor 108 in a position for capturing a specific type of image. The first sensor positioner 601, illustrated in FIG. 6A, includes a backplate 603 and a pressure arm 605. To selectively couple the imaging sensor 108 to the first sensor positioner 601, the imaging sensor 108 is placed between the backplate 603 and the pressure arm 605. The imaging sensor 108 is held in place by the shape of the backplate 603 and friction/pressure applied by the pressure arm 605. A first permanent magnet 607 is also included in the first sensor position at a location proximal to the imaging sensor 108 when coupled to the sensor positioner 601. The first permanent magnet 607 creates a magnetic field of a known magnitude and vector direction that is detectable by the magnetometer 129 of the imaging sensor 108 when the imaging sensor is coupled to the first sensor positioner 601.

Figure 6B:
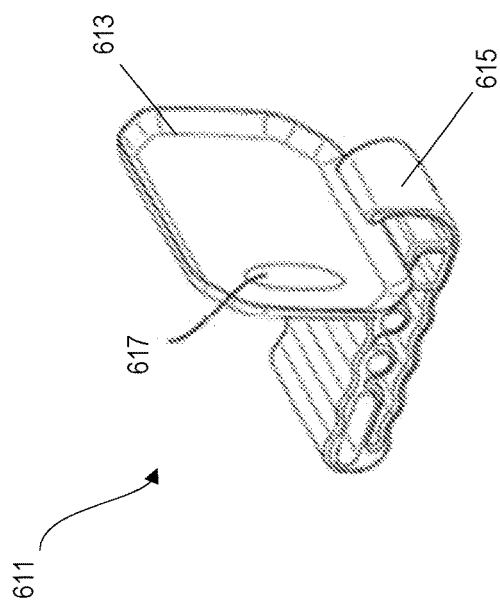
FIG. 6B is a perspective view of a second sensor positioner for holding the imaging sensor in a second position for capturing an image.

The second sensor positioner 611, illustrated in FIG. 6B, also includes a backplate 613 and a pressure arm 615 for selectively coupling the imaging sensor 108 to the second sensor positioner 611. The shape and arrangement of the second sensor positioner 611 is different from that of the first sensor positioner 601 and is configured for placing the imaging sensor for capturing images of dental structures at a different location in a patient's mouth. The second sensor positioner 611 also includes a second permanent magnet 617. The second permanent magnet 617 also generates a magnetic field of a known magnitude and vector direction that is detectable by the imaging sensor 108 when coupled to the second sensor positioner 611. However, due to the type and positioning of the second permanent magnet 617, the magnetic field generated by the second permanent magnet 617 and detected by the magnetometer 129 of the imaging sensor 108 when coupled to the second sensor positioner 611 is different from the magnetic field that is generated by the first permanent magnet 607 and detected by the magnetometer 129 when the imaging sensor 108 is coupled to the first sensor positioner 601. Based on these different and known magnetic fields, the imaging system 102 is configured to identify, based on the output of the magnetometer 129, when the imaging sensor 108 is coupled to a sensor positioner and to identify whether the imaging sensor 108 is coupled to the first sensor positioner 601 or to the second sensor positioner 611.

Figure 6A:
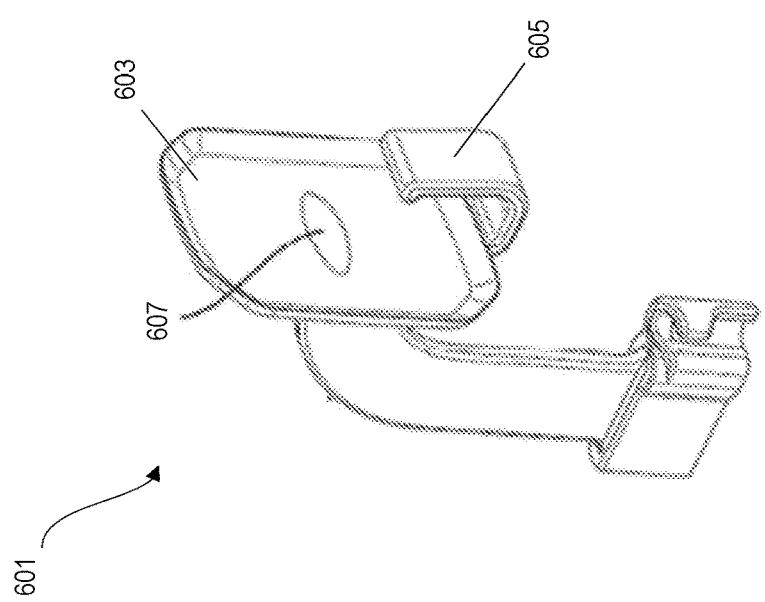
FIG. 6A is a perspective view of a sensor positioner for holding an imaging sensor in a first position for capturing an image.

Although the examples illustrated in FIGS. 6A and 6B show the permanent magnet 607, 617 positioned in or on the backplate 603, 613, in other implementations and in other sensor positioners, the permanent magnet can be positioned in other fixed locations. For example, a permanent magnet may be positioned on the pressure arm 615 or on another structural portion of the sensor positioner behind or below the backplate 613.

As illustrated in FIG. 7, a magnetic field applied by a permanent magnet integrated into a sensor positioner can govern a transition from the "ready" state into the "armed" state and, in some implementations where multiple different sensor positioners and/or sensor positioner configurations are used to capture a series of images, the detected magnetic field can be used to provide automated instructions to a user of the imaging system 100. While the imaging sensor 108 is operating in a "ready" mode (block 701), the output of the magnetometer 129 is analyzed to determine a magnitude and vector direction of a magnetic field (block 703). The detected magnetic field is analyzed to determine whether the detected magnetic field indicates a coupling with a sensor positioner (block 705). If not, then the imaging sensor 108 continues to operate in the "ready" state (block 701). However if the detected magnetic field is indicative of coupling with a sensor positioner (block 705), then the type and/or configuration of the sensor positioner is identified based on the magnitude and vector direction of the detected magnetic field (block 707). In response, the imaging sensor 108 is armed (block 709) and, in some implementations, an instruction for placement of the imaging sensor 108 is displayed on the graphical user interface of the imaging system controller computer 101. After an image is captured (based, for example, on a user-activated or automated trigger) (block 711), the graphical user interface of the imaging system controller computer 101 outputs an instruction for a next image to be captured (block 713). In some embodiments, the instruction is output as a text instruction shown on the display 106 while, in other embodiments, the instruction is output audibly through a speaker.

In some embodiments, the output instruction also indicates whether a new sensor positioner or a new configuration is required for the next image to be captured. If the same sensor positioner and the same configuration is to be used for the next image (block 715), the imaging sensor 108 remains in the "armed" state and the next image is captured (block 711). However, if a different sensor positioner or a different configuration is needed for the next image (block 715), then the imaging sensor 108 is disarmed (block 717) and the detected magnetic field is again monitored until a magnetic field is identified that is indicative of a coupling between the imaging sensor housing 109 and the sensor positioner (block 705).

Although the example of FIG. 7 describes a transition from a "ready" state into an "armed" state, in other implementations, the magnetic field applied by a permanent magnetic incorporated into the sensor positioner can instead govern other types of state transitions including, for example, a transition from one "ready" state into another "ready" state, from one "armed" state into another "armed" state, or from a "low power" state to a "ready" state.

Figure 8:
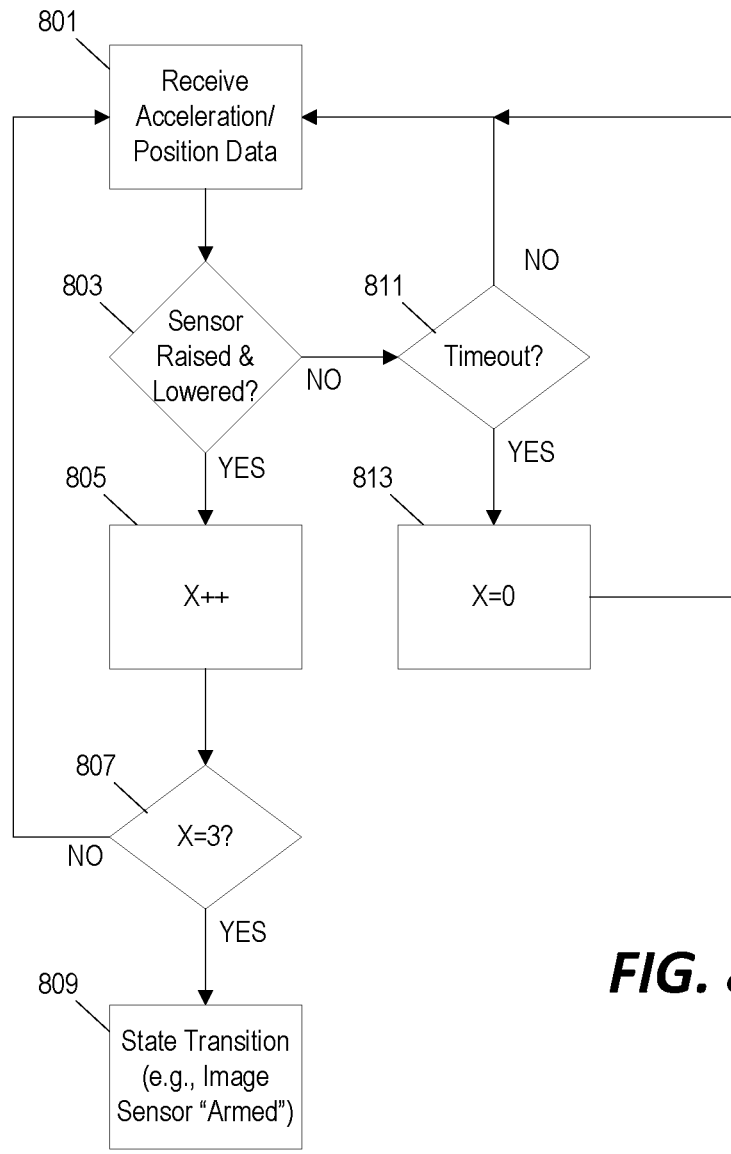
FIG. 8 is a flowchart of a method for transitioning between operating states of the imaging system of FIG. 1A based on a detection of a specific movement of the imaging sensor based on an output of the multi-dimensional sensor.

In some implementations, the transition from the "ready" state into the "armed" state can be governed based on outputs from other sensor components of the imaging sensor 108. For example, specific gestures made with the imaging sensor housing 109 can be detected based on the output from the accelerometer 125 and/or the gyroscopic sensor 127 and used to transition from the "ready" state into the "armed" state. This type of gesture detection can also be used to control the state of application software. FIG. 8 illustrates a method for detecting one example of a specific gesture that can trigger a transition from a "ready" state into an "armed" state. In this example, the imaging sensor 108 is transitioned into the "armed" state if the imaging sensor 108 is raised and lowered three times in succession.

Acceleration and/or position data is received from the accelerometer 125 and/or the gyroscopic sensor 127, respectively, (block 801) and is analyzed to determine whether a "raise & lower" gesture has been made with the imaging sensor 108 (block 803). If so, a counter is incremented (block 805) and, if the counter has not yet been incremented to three (3) (block 807), the imaging system 100 continues to monitor the acceleration/position data (block 801) to detect additional "raise and lower" gestures (block 803). When three successive "raise and lower" gestures are detected and the counter has been incremented to three (block 807), then the imaging sensor 108 is transitioned from the "ready" state into the "armed" state (block 809).

To ensure that the three "raise and lower" gestures are made in deliberate succession, a timeout mechanism is applied. If a timeout period has not yet elapsed since the first "raise and lower" gesture was detected (or, in some implementations, since the most recent "raise and lower" gesture was detected) (block 811), the imaging system 100 continues to monitor the acceleration/position data (block 801) to detect additional "raise and lower" gestures (block 803). However, if the timeout period has expired (block 811), then the counter is reset to zero (block 813). The detection of specific gestures and movements can also be used to trigger other operations of the imaging system including, for example, resetting a dark current.

FIG. 8 illustrates only one example of a gesture that can be performed with the imaging sensor 108 and detected based on the outputs from the various sensors within the imaging sensor housing 109. In other implementations, the imaging system 100 is configured to detect other types of gestures instead of three successive "raise and lower" gestures. In some implementations, different gestures can be used to not only trigger a transition into the "armed" state, but also to indicate to the imaging system 100 which specific type of image (or image series) is to be captured by the imaging system 100. For example, detection of a first gesture pattern indicates to the imaging system 100 that a first type of x-ray image is to be captured and, in response, the graphical user interface of the imaging system controller computer 101 outputs instructions and information relevant specifically to the first type of x-ray image. Conversely, detection of a second, different gesture pattern indicates to the imaging system 100 that a second type of x-ray image is to be captured and, in response, the graphical user interface of the imaging system controller computer 101 outputs instructions and information relevant specifically to the second type of x-ray image or image series. Alternatively, the imaging system controller computer 101 may process or store the captured image data differently based on which image type is indicated by the detected gesture pattern.

Figure 9:
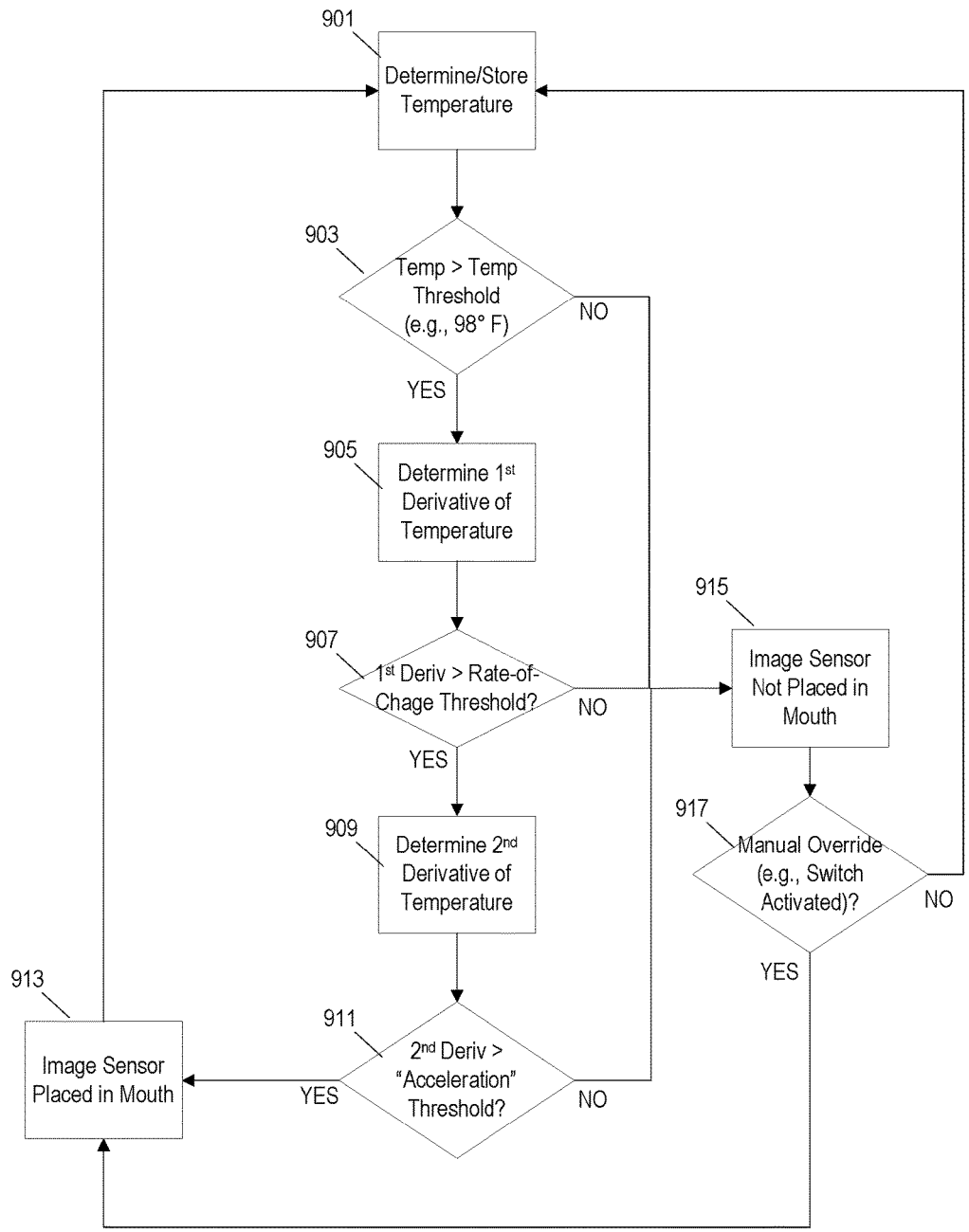
FIG. 9 is a flowchart of a method for detecting when the imaging sensor of the imaging system of FIG. 1A is placed in the mouth of a patient based on an output of the multi-dimensional sensor.

In some implementations, the imaging system 100 may also be configured to transition from one state to another by detecting when the imaging sensor 108 has likely been placed within the mouth of a patient. FIG. 9 illustrates a method of determining whether the imaging sensor 108 has been placed within the mouth of a patient based on an output from the temperature sensor 131. Because the temperature detected by the temperature sensor 131 will likely increase when the imaging sensor 108 is placed in the mouth of a patient, the imaging system 100 applies three different temperature-based criteria to confirm that the imaging sensor 108 has been moved from a position outside of the patient's mouth to a new position within the patient's mouth.

First, the imaging system 100 determines and stores a temperature reading based on the output of the temperature sensor 131 (block 901). The present temperature is compared to a temperature threshold (for example, 98° F.) (block 903). If the imaging sensor 108 has been placed in the mouth of a patient, then the sensed temperature should exceed this temperature threshold.

Second, the imaging system 100 determines a first derivative of sensed temperatures based on the most recently detected temperature and previously detected temperatures stored on a memory (for example, memory 105 or sensor memory 119) (block 905). The calculated first derivative of the temperature is compared to a rate-of-change threshold (block 907). If the imaging sensor 108 has been moved from a position outside of a patient's mouth (at room temperature) to a position inside the patient's mouth (at "body" temperature), then the calculated first derivative should exceed this rate-of-change threshold.

Third, the imaging system 100 determines a second derivative of sensed temperatures (block 909). This second derivative is indicative of how quickly the rate-of-change of the temperature is increasing and is compared to an "acceleration" threshold (block 911). Again, if the imaging sensor 108 has been moved from a position outside of the patient's mouth (at room temperature) to a position inside the patient's mouth (at "body" temperature), then the calculated second derivative should indicate a sudden increase in the rate of temperature change and should exceed this acceleration threshold.

If all three temperature-based criteria are satisfied, the imaging sensor 108 is transitioned into the "armed" state based on the assumption that the imaging sensor 108 has been placed inside a patient's mouth (block 913). However, if any one of the three criteria is not satisfied, the imaging system 100 cannot "confirm" that the imaging sensor 108 has been placed inside a patient's mouth and, therefore, the imaging sensor 108 remains in the "ready" state (block 915). Due to ambient temperature fluctuations, some methods for determining whether an imaging sensor 108 has been placed in the mouth of a patient based on sensed temperatures may result in false "negatives" causing the imaging sensor 108 to remain in the "ready" state even after the imaging sensor 108 has actually been placed in the mouth of the patient. In some embodiments, the user can override a false negative and force the imaging sensor 108 to transition into the "armed" state using a switch or input on the graphical user interface of the imaging system controller computer 101 (block 917).

As discussed above in reference to FIGS. 2A-2E, the imaging system 100 may be configured to apply one or more error condition check routines when the imaging sensor 108 is first connected to the imaging system controller computer 101, in response to (or in preparation for) a state transition, or periodically while operating in a particular state. In some implementations, the imaging sensor 108 is equipped with one or more additional internal sensors that are configured for other types of error condition detection. For example, FIG. 9 illustrates a method for detecting potential damage to the imaging sensor housing 109 due to sudden impact on the housing or biting of the housing by a patient based on an air pressure within the imaging sensor housing 109 detected by the air pressure sensor 135.

Figure 10:
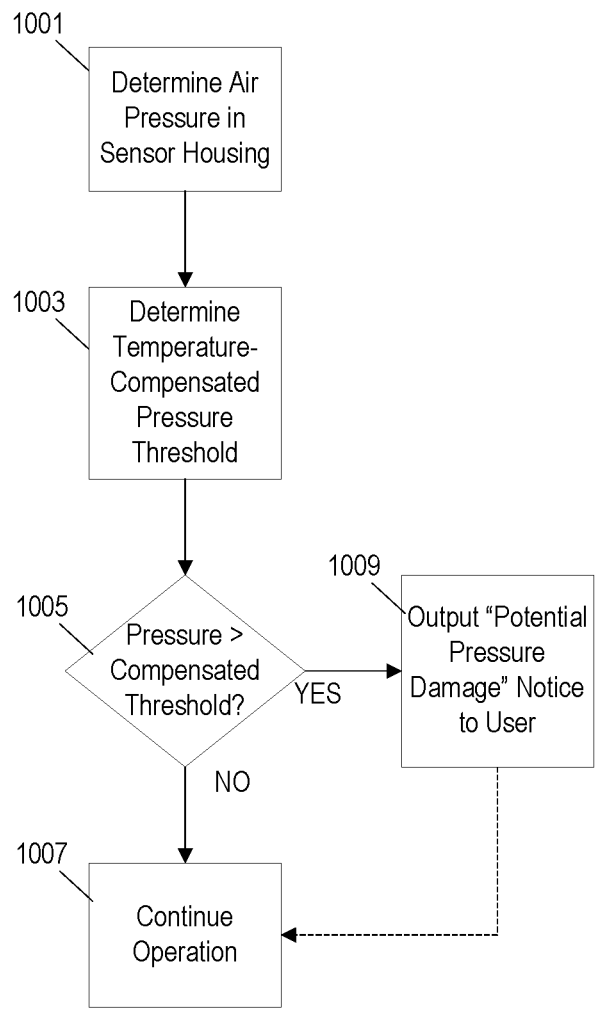
FIG. 10 is a flowchart of a method for detecting possible damage to the sensor housing in the imaging system of FIG. 1A based on an air pressure detected by the multi-dimensional sensor.

In the example of FIG. 10, the imaging system 100 monitors the output of the air pressure sensor 135 (block 1001). Because air pressures will change naturally due to changes in temperature, the imaging system 100 determines a temperature-compensated pressure threshold (block 1003) and compares the detected air pressure to the compensated threshold (block 1005). If the detected air pressure remains below the compensated threshold, then the imaging system 100 continues its operation (block 1007). However, an air pressure that is above the compensated threshold may be caused by biting of the imaging sensor housing 109 or another potential damaging impact. Therefore, in response to detecting an air pressure above the compensated threshold (block 1005), the imaging system 100 outputs a "Potential Pressure Damage" notice to the user on the graphical user interface of the imaging system controller computer 101 (block 909). In some implementations, this notice instructs the user to visually inspect the imaging sensor housing 109 for damage. In other implementations, the imaging system 100 is configured to run an automated check routine in response to detecting an air pressure indicative of potential damage and, depending on the result of the automated check routine, will either apply an automated self-correction or output a notice to the user with further instructions.

In the example of FIG. 10, even after detecting an increased air pressure indicative of a possible damage event, the imaging system 100 continues its operation (block 1007) and relies upon the user to determine whether the imaging sensor housing 109 has been damaged to the extent that usage of the imaging sensor 108 should be stopped. However, in other implementations, the imaging system 100 may be configured to disable the imaging sensor 108 in response to detection of the possible damage event or to take additional mitigating action before continuing operation. For example, the imaging system 100 may be configured to automatically transmit a notice to a technical support system requesting more substantial inspection or testing of the imaging sensor 108 in response to detecting an air pressure that exceeds the compensation threshold. In other implementations, the imaging system 100 may be configured to automatically initiate the error condition check routine (for example, one or more of the routines illustrated in FIGS. 2A through 2E) in response to detection of an air pressure that exceeds the compensation threshold.

In still other implementations, the imaging system 100 may apply multiple air pressure thresholds each triggering a different mitigating action. For example, the imaging system 100 may be configured to output a notice on the graphical user interface instructing the user to visually inspect the imaging sensor housing 109 if a first pressure threshold is exceeded, to apply the error condition check routine of FIGS. 2A through 2E if a second (higher) pressure threshold is exceeded, and to disable the imaging sensor 108 until it is thoroughly inspected by technical support personnel if a third (highest) threshold is exceeded.

Figure 11:
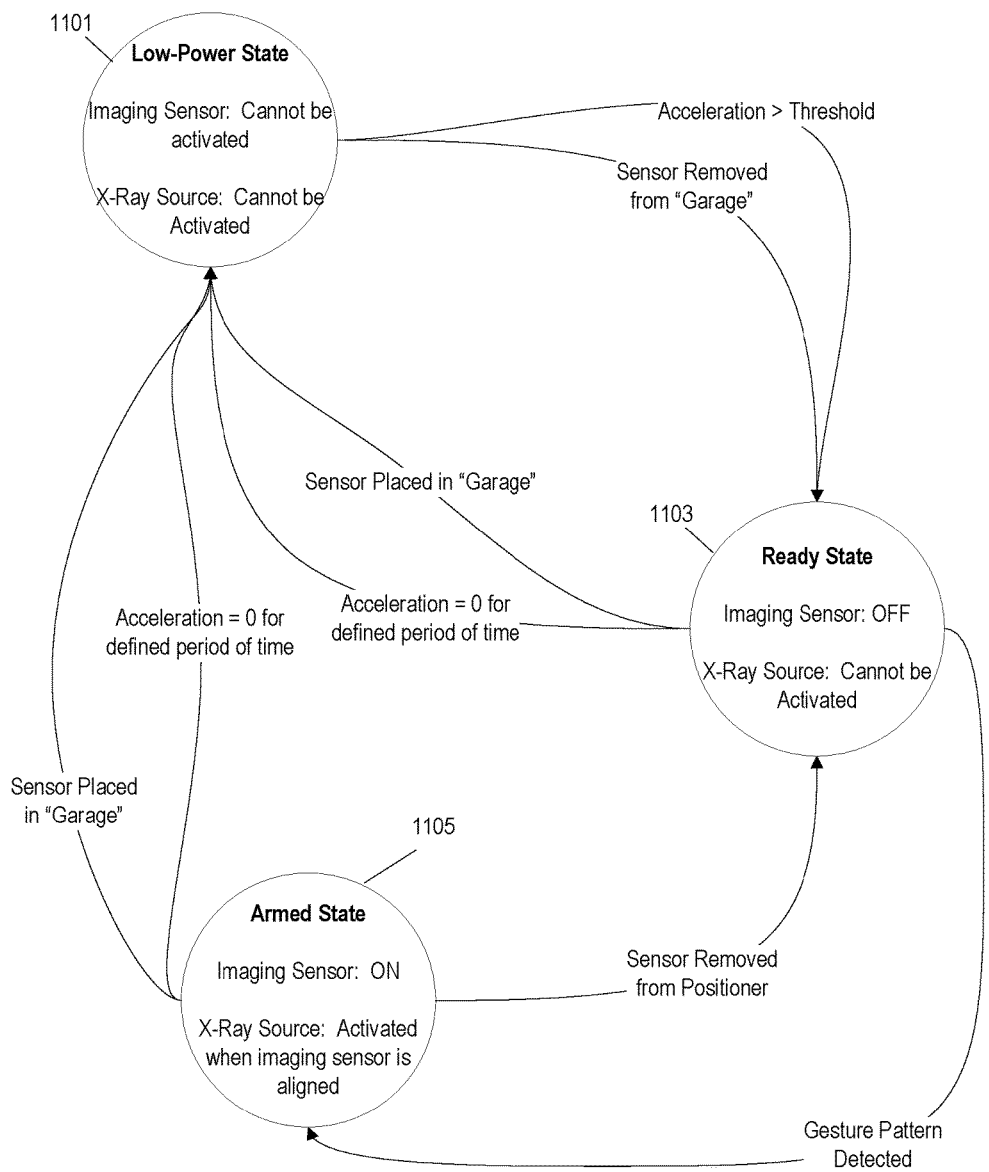
FIG. 11 is a state diagram of transitions between multiple operating states in the imaging system of FIG. 1A based on outputs from the multi-dimensional sensor.

The systems and methods described above provide examples of methods implemented by the imaging system 100 for detecting error conditions and for transitioning between states that govern the operation of an imaging sensor 108. FIG. 11 provides a specific example of a state diagram illustrating the interaction of various methods and systems described above for controlling and regulating the operation of the imaging sensor 108. In the example of FIG. 11, the imaging sensor 108 is operated in one of three states: a low power state, a ready state, and an armed state.

When operating in the low power state 1101, the imaging sensor 108 cannot be activated—that is the imaging sensor 108 cannot capture image data—and the x-ray source 107 cannot be activated to emit x-ray radiation. In some implementations, some of the other sensor and/or logic components of the imaging sensor 108 are also turned off or powered down when the imaging sensor 108 is operating in the low-power state.

When operating in the ready state 1103, the image sensor array 115 is turned OFF, but can be activated (i.e., operated to capture image data) upon a transition from the ready state 1103 into the armed state 1105. In the example of FIG. 11, the imaging sensor 108 cannot transition directly from the low-power state 1101 into the armed state 1105.

When operating in the armed state 1105, the image sensor array 115 is turned on and will capture image data in response to a user-activated or an automated trigger. In the example of FIG. 11, the x-ray source 107 can be activated to emit x-rays when the imaging sensor 108 is operating in the armed state 1105 and when the output of the multi-dimensional sensor 123 indicates that the imaging sensor 108 is aligned with the x-ray source 107.

When operating in the low-power state 1101, the imaging sensor 108 can transition into the ready state 1103 in response to detecting that the imaging sensor 108 has been removed from the "garage" 303 (for example, the method of FIG. 4) or in response to detecting an acceleration that exceeds a threshold (for example, the method of FIG. 5). In the example of FIG. 11, the imaging sensor 108 cannot transition directly into the armed state 1105 when operating in the low-power state 1101.

When operating in the ready state 1103, the imaging sensor 108 can transition into the armed state 1105 in response to detecting a gesture pattern (for example, the method of FIG. 8). The imaging sensor 108 can also transition from the ready state 1103 into the low-power state 1101 in response to detecting placement of the imaging sensor 108 in the "garage" 303 (for example, the method of FIG. 4) or in response to detecting an acceleration equal to zero for a defined period of time (for example, the method of FIG. 5).

When operating in the armed state 1105, the imaging sensor 108 can be operated to capture x-ray image data. The imaging sensor 108 can transition from the armed state 1105 into the ready state 1103 in response to detecting that the imaging sensor 108 has been removed from a sensor positioner (for example, the method of FIG. 7). In the example of FIG. 11, the imaging sensor 108 can also transition directly from the armed state 1105 into the low-power state 1101 in response to detecting that the imaging sensor 108 has been placed in the storage "garage" 303 (for example, the method of FIG. 4) or in response to detecting an acceleration equal to zero for a defined period of time (for example, the method of FIG. 5).

In some imaging systems 100 implementing the state diagram of FIG. 11, the imaging system 100 may be configured to perform one or more of the error condition check routines described above in reference to FIGS. 2A through 2E and FIG. 10 when the imaging sensor 108 transitions from the ready state 1103 into the armed state 1105. In some implementations, the imaging system 100 also performs one or more of these error condition check routines either periodically while operating in the armed state 1105 or after capturing a defined number (for example, one or more) of x-ray images while operating in the armed state 1105.

FIG. 11 is only one example of a state diagram that may be implemented by an imaging system 100. In other implementations, the imaging system 100 may implement more operating states including one or more "low-power" states, one or more "ready" states, and one or more "armed" states. In other implementations, more, fewer, or different criteria may be used to initiate transitions from one operating state to another.

Also, the examples discussed above describe the "imaging system 100" monitoring the outputs from the sensor components of the imaging sensor 108 and determining whether to initiate a state transition. Accordingly, in various different embodiments, these and other methods may be executed by one or more of the various processors included in the imaging system 100 or other processing systems communicative coupled to the imaging system 100. For example, in some implementations, the methods for analyzing the sensor outputs, determining when to initiate a state transition, and performing an error condition check routine are provided by the electronic processor 103 of the imaging system controller computer 101 executing instructions stored on the memory 105. However, in other implementations, these methods are provided by the sensor electronic processor 117 executing instructions stored on the sensor memory 119. In still other implementations, some of the methods are performed by the electronic processor 103 of the imaging system controller computer 101 while other methods are performed by the sensor electronic processor 117 or methods are performed cooperatively by instructions executed on both the sensor electronic processor 117 and the electronic processor 103 of the imaging system controller computer 101.

Finally, although several of the methods illustrated in the attached drawings and discussed in the examples above are described as "sub-routines," in other implementations, one or more of these methods may be implemented as a looped process. For example, one or more of the individual methods illustrated in FIGS. 2B, 2C, 2D, 2E, 4, 5, and 10 can be implemented as processes that continually repeat execution upon completion of each iteration or after a defined time delay. Furthermore, in some implementations, multiple individual looped processes can be implemented to execute in parallel as separate individual loops.

Thus, the invention provides, among other things, imaging systems configured to transition an imaging sensor between multiple operating states, including a low-power state, based on outputs from sensor components integrated into an imaging sensor housing. Various features and advantages of the invention are set forth in the following claims.

What is claimed is:

1. A method for determining that an intra-oral imaging sensor is positioned in a mouth of a patient, the intra-oral imaging sensor including a temperature sensor, the method comprising:
   receiving, by an electronic processor, an output from the temperature sensor indicative of a sensed temperature; and
   determining that the intra-oral imaging sensor is positioned in the mouth of the patient based at least in part on the output from the temperature sensor.

2. The method of claim 1, further comprising comparing, by the electronic processor, the sensed temperature to a temperature threshold, and
   wherein determining that the intra-oral imaging sensor is positioned in the mouth of the patient includes determining that the intra-oral imaging sensor is positioned in the mouth of the patient based at least in part on the comparison of the sensed temperature to the temperature threshold.

3. The method of claim 1, further comprising:
   determining, by the electronic processor, a rate of change of the sensed temperature; and
   comparing the rate of change of the sensed temperature to a rate-of-change threshold,
   wherein determining that the intra-oral imaging sensor is positioned in the mouth includes determining that the intra-oral imaging sensor has been moved from outside of the mouth to inside of the mouth when the rate of change of the sensed temperature exceeds the rate-of-change threshold.

4. The method of claim 3, further comprising:
   monitoring, by the electronic processor, the output of the temperature sensor over a period of time; and
   determining a plurality of sensed temperatures in a sequence of sensed temperatures based at least in part on the monitored output of the temperature sensor over the period of time,
   wherein determining the rate of change of the sensed temperature includes determining a first derivative of the sequence of sensed temperatures, and wherein comparing the rate of change of the sensed temperature to the rate-of-change threshold includes comparing the first derivative of the sequence of sensed temperatures to the rate-of-change threshold.

5. The method of claim 4, further comprising comparing the sensed temperature to a temperature threshold, and wherein determining that the intra-oral imaging sensor is positioned in the mouth of the patient includes determining that the intra-oral imaging sensor has been moved from outside of the mouth to inside of the mouth when both
the sensed temperature exceeds the temperature threshold and
the first derivative of the sequence of sensed temperatures exceeds the rate-of-change threshold.

6. The method of claim 1, further comprising:
monitoring, by the electronic processor, the output of the temperature sensor over a period of time;
determining a plurality of sensed temperatures in a sequence of sensed temperatures based at least in part on the monitored output of the temperature sensor over the period of time;
determining a second derivative of the sequence of sensed temperatures; and
comparing, by the electronic processor, the second derivative of the sequence of sensed temperatures to a temperature acceleration threshold,
wherein determining that the intra-oral imaging sensor is positioned in the mouth of the patient includes determining that the intra-oral imaging sensor has been moved from outside of the mouth to inside of the mouth when the second derivative of the sequence of sensed temperatures exceeds the temperature acceleration threshold.

7. The method of claim 1, further comprising:
monitoring, by the electronic processor, the output of the temperature sensor over a period of time;
determining a plurality of sensed temperatures in a sequence of sensed temperatures based at least in part on the monitored output of the temperature sensor over the period of time;
determining a current temperature based on a most recent output of the temperature sensor;
determining a first derivative of the sequence of sensed temperatures, the first derivative being indicative of a rate of change of the sensed temperature over the period of time;
determining a second derivative of the sequence of sensed temperature, the second derivative being indicative of a rate at which the rate of change of the sensed temperature is changing over the period of time;
comparing, by the electronic processor, the current temperature to a temperature threshold;
comparing, by the electronic processor, the first derivative of the sequence of sensed temperatures to a rate-of-change threshold; and
comparing, by the electronic processor, the second derivative of the sequence of sensed temperatures to a temperature acceleration threshold,
wherein determining that the intra-oral imaging sensor is positioned in the mouth of the patient includes determining that the intra-oral imaging sensor has been moved from outside of the mouth to inside of the mouth in response to determining that at least three defined conditions are simultaneously satisfied, wherein the three defined conditions include
the current temperature exceeds the temperature threshold,
the first derivative of the sequence of sensed temperatures exceeds the rate-of-change threshold, and
the second derivative of the sequence of sensed temperatures exceeds the temperature acceleration threshold.

8. The method of claim 1, further comprising:
transitioning the intra-oral imaging sensor from a first operating state into a second operating state in response to determining that the intra-oral imaging sensor is positioned in the mouth of the patient; and
operating the intra-oral imaging sensor in the second operating state until a separate state transition criteria is satisfied.

9. The method of claim 8, further comprising:
receiving a manual override signal from a user interface; and
transitioning the intra-oral imaging sensor from the first operating state into the second operating state in response to receiving the manual override signal regardless of the output of the temperature sensor.

10. The method of claim 1, further comprising:
selectively operating the imaging system in each of a plurality of different operating states;
automatically altering, by the electronic processor, the operating state of the imaging system in response to determining that the intra-oral imaging sensor is positioned in the mouth of the patient; and
automatically altering, by the electronic processor, the operating state of the imaging system based at least in part on an output from a multi-dimensional sensor, wherein the multi-dimensional sensor is at least partially housed within a housing of the intra-oral imaging sensor and includes a three-dimensional accelerometer, a three-dimensional gyroscope, and a three-dimensional magnetometer.

11. The imaging system of claim 1, wherein the electronic processor is further configured to
monitor the output of the temperature sensor over a period of time,
determine a plurality of sensed temperatures in a sequence of sensed temperatures based at least in part on the monitored output of the temperature sensor over the period of time,
determine a current temperature based on a most recent output of the temperature sensor,
determine a first derivative of the sequence of sensed temperatures, the first derivative being indicative of a rate of change of the sensed temperature over the period of time,
determine a second derivative of the sequence of sensed temperatures, the second derivative being indicative of a rate at which the rate of change of the sensed temperature is changing over the period of time,
compare the current temperature to a temperature threshold,
compare the first derivative of the sequence of sensed temperatures to a rate-of-change threshold, and
compare the second derivative of the sequence of sensed temperatures to a temperature acceleration threshold,
wherein the electronic processor is configured to determine that the intra-oral imaging sensor is positioned in the mouth of the patient by determining that the intra-oral imaging sensor has been moved from outside of the mouth to inside of the mouth in response to determining that at least three defined conditions are simultaneously satisfied, wherein the at least three defined conditions include the current temperature exceeds the temperature threshold, the first derivative of the sequence of sensed temperatures exceeds the rate-of-change threshold, and the second derivative of the sequence of sensed temperatures exceeds the temperature acceleration threshold.

12. An imaging system comprising:
an intra-oral imaging sensor including an image sensing component and a temperature sensor; and
an electronic processor configured to
receive an output from the temperature sensor indicative of a sensed temperature, and
determine that the intra-oral imaging sensor is positioned in the mouth of the patient based at least in part on the output of the temperature sensor.

13. The imaging system of claim 12, wherein the electronic processor is further configured to compare the sensed temperature to a temperature threshold, and wherein the electronic processor is configured to determine that the intra-oral imaging sensor is positioned in the mouth of the patient by determining that the intra-oral imaging sensor is positioned in the mouth of the patient based at least in part on a comparison of the sensed temperature to the temperature threshold.

14. The imaging system of claim 12, wherein the electronic processor is further configured to
determine a rate of change of the sensed temperature, and
compare the rate of change of the sensed temperature to a rate-of-change threshold,
wherein the electronic processor is configured to determine that the intra-oral imaging sensor is positioned in the mouth of the patient by determining that the intra-oral imaging sensor has been moved from outside the mouth to inside of the mouth when the rate of change of the sensed temperature exceeds the rate-of-change threshold.

15. The imaging system of claim 14, wherein the electronic processor is further configured to
monitor the output of the temperature sensor over a period of time, and
determining a plurality of sensed temperatures in a sequence of sensed temperatures based at least in part on the monitored output of the temperature sensor over the period of time,
wherein the electronic processor is configured to determine the rate of change of the sensed temperature by determining a first derivative of the sequence of sensed temperatures, and
wherein the electronic processor is configured to compare the rate of change of the sensed temperature to the rate-of-change threshold by comparing the first derivative of the sequence of sensed temperatures to the rate-of-change threshold.

16. The imaging system of claim 15, wherein the electronic processor is further configured to compare the sensed temperature to a temperature threshold, and wherein the electronic processor is configured to determine that the intra-oral imaging sensor is positioned in the mouth of the patient by determining that the intra-oral sensor has been moved from outside of the mouth to inside of the mouth when both
the sensed temperature exceeds the temperature threshold and
the first derivative of the sequence of sensed temperatures exceeds the rate-of-change threshold.

17. The imaging system of claim 12, wherein the electronic processor is further configured to
monitor the output of the temperature sensor over a period of time,
determine a plurality of sensed temperatures in a sequence of sensed temperatures based at least in part on the monitored output of the temperature sensor over the period of time,
determine a second derivative of the sequence of sensed temperatures, and
compare the second derivative of the sequence of sensed temperatures to a temperature acceleration threshold,
wherein the electronic processor is configured to determine that the intra-oral imaging sensor is positioned in the mouth of the patient by determining that the intra-oral imaging sensor has been moved from outside of the mouth to inside of the mouth when the second derivative of the sequence of sensed temperatures exceeds the temperature acceleration threshold.

18. The imaging system of claim 12, wherein the electronic processor is further configured to
transition the intra-oral imaging sensor from a first operating state into a second operating state in response to determining that the intra-oral imaging sensor is positioned in the mouth of the patient; and
operate the intra-oral imaging sensor in the second operating state until a separate state transition criteria is satisfied.

19. The method of claim 18, further comprising a user interface configured to generate a manual override signal in response to a user input, wherein the electronic processor is further configured to
receive the manual override signal from the user interface, and
transition the intra-oral imaging sensor from the first operating state into the second operating state in response to receiving the manual override signal regardless of the output of the temperature sensor.

20. The imaging system of claim 12, wherein the intra-oral imaging sensor further includes a housing and a multi-dimensional sensor at least partially housed within the housing, the multi-dimensional sensor including a three-dimensional accelerometer, a three-dimensional gyroscope, and a three-dimensional magnetometer,
wherein the electronic processor is further configured to
selectively operate the imaging system in each of a plurality of different operating states,
alter the operating state of the imaging system in response to determining that the intra-oral imaging sensor is positioned in the mouth of the patient, and
alter the operating state of the imaging system based at least in part on an output from the multi-dimensional sensor.

* * * * *